(12) United States Patent
Yamaguchi et al.

(10) Patent No.: US 8,803,106 B2
(45) Date of Patent: Aug. 12, 2014

(54) OPTICAL ANALYSIS DEVICE, OPTICAL ANALYSIS METHOD AND COMPUTER PROGRAM FOR OPTICAL ANALYSIS FOR OBSERVING POLARIZATION CHARACTERISTICS OF A SINGLE LIGHT-EMITTING PARTICLE

(71) Applicant: Olympus Corporation, Tokyo (JP)

(72) Inventors: Mitsushiro Yamaguchi, Hachioji (JP); Tetsuya Tanabe, Setagaya-ku (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/864,867

(22) Filed: Apr. 17, 2013

(65) Prior Publication Data

US 2013/0228706 A1 Sep. 5, 2013

Related U.S. Application Data

(63) Continuation of application No. PCT/JP2011/072939, filed on Oct. 5, 2011.

(30) Foreign Application Priority Data

Oct. 19, 2010 (JP) ................. 2010-234769

(51) Int. Cl.
*G01J 1/58* (2006.01)
*G01N 21/64* (2006.01)
*G02B 21/00* (2006.01)

(52) U.S. Cl.
CPC ........ *G01N 21/6445* (2013.01); *G01N 21/6458* (2013.01); *G02B 21/0092* (2013.01)
USPC .................... 250/459.1; 250/458.1

(58) Field of Classification Search
USPC ........................................... 250/459.1, 458.1
See application file for complete search history.

(56) References Cited

U.S. PATENT DOCUMENTS 3,887,812 A 6/1975 Hirschfeld
(Continued)

FOREIGN PATENT DOCUMENTS

EP 1906172 A1 4/2008
(Continued)

OTHER PUBLICATIONS

Masataka Kinjo, "Single molecule protein, nucleic acid, and enzyme assays and their procedures Single molecule detection by fluorescence correlation spectroscopy", Protein, Nucleic acid Enzyme vol. 44, No. 9, 1999, pp. 1431-1438. (cited in specification; w/English trans).

(Continued)

*Primary Examiner* — David Porta
*Assistant Examiner* — Djura Malevic
(74) *Attorney, Agent, or Firm* — Westerman, Hattori, Daniels & Adrian, LLP

(57) ABSTRACT

There is provided an optical analysis technique which observes a polarization characteristic of a light-emitting particle using the scanning molecule counting method using an optical measurement with a confocal microscope or a multiphoton microscope. In the inventive optical analysis technique, the light detection region is irradiated with excitation light consisting of predetermined polarized light component(s) and the intensity of at least one polarized light component of the light from the light detection region is detected with moving the position of the light detection region of the optical system in a sample solution; a signal of each light-emitting particle is detected individually in the intensity of at least one polarized light component; and based on the intensity of at least one polarized light component of the signal of the detected light-emitting particle, the polarization characteristic value of the light-emitting particle is computed.

26 Claims, 7 Drawing Sheets

(56) References Cited

U.S. PATENT DOCUMENTS

Figure 2A:
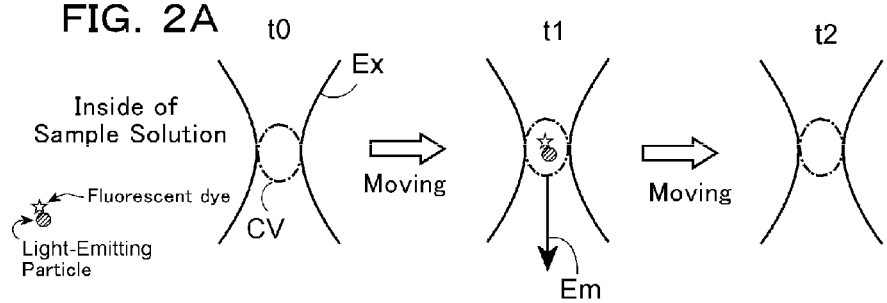

| | | | |
|---|---|---|---|
| 4,251,733 A | 2/1981 | Hirleman, Jr. | |
| 5,011,279 A | 4/1991 | Auweter et al. | |
| 5,866,336 A | 2/1999 | Nazarenko et al. | |
| 5,949,532 A | 9/1999 | Schrof et al. | |
| 6,280,960 B1* | 8/2001 | Carr | 435/7.2 |
| 6,376,843 B1 | 4/2002 | Palo | |
| 6,388,746 B1* | 5/2002 | Eriksson et al. | 356/318 |
| 6,388,788 B1 | 5/2002 | Harris et al. | |
| 6,400,487 B1 | 6/2002 | Harris et al. | |
| 6,403,338 B1* | 6/2002 | Knapp et al. | 435/91.2 |
| 6,710,871 B1* | 3/2004 | Goix | 356/318 |
| 6,856,391 B2* | 2/2005 | Garab et al. | 356/366 |
| 6,927,401 B1 | 8/2005 | Palo | |
| 7,330,255 B2 | 2/2008 | Cluzel et al. | |
| 8,264,684 B2* | 9/2012 | Livingston | 356/337 |
| 8,284,484 B2 | 10/2012 | Hoult et al. | |
| 2001/0035954 A1 | 11/2001 | Rahn et al. | |
| 2002/0008211 A1 | 1/2002 | Kask | |
| 2002/0036775 A1 | 3/2002 | Wolleschensky et al. | |
| 2003/0036855 A1 | 2/2003 | Harris et al. | |
| 2003/0218746 A1 | 11/2003 | Sampas | |
| 2004/0022684 A1* | 2/2004 | Heinze et al. | 422/82.08 |
| 2004/0051051 A1 | 3/2004 | Kato et al. | |
| 2004/0150880 A1 | 8/2004 | Nakata et al. | |
| 2005/0260660 A1 | 11/2005 | van Dongen et al. | |
| 2006/0078998 A1 | 4/2006 | Puskas et al. | |
| 2006/0158721 A1 | 7/2006 | Nakata et al. | |
| 2006/0256338 A1 | 11/2006 | Gratton et al. | |
| 2008/0052009 A1 | 2/2008 | Chiu et al. | |
| 2008/0117421 A1 | 5/2008 | Yamaguchi et al. | |
| 2009/0159812 A1 | 6/2009 | Livingston | |
| 2010/0033718 A1 | 2/2010 | Tanaami | |
| 2010/0177190 A1 | 7/2010 | Chiang et al. | |
| 2010/0202043 A1 | 8/2010 | Ujike | |
| 2010/0301231 A1 | 12/2010 | Yamaguchi | |
| 2012/0319009 A1 | 12/2012 | Yamaguchi et al. | |
| 2013/0048875 A1 | 2/2013 | Yamaguchi et al. | |
| 2013/0228705 A1 | 9/2013 | Nishikawa et al. | |

FOREIGN PATENT DOCUMENTS

| | | |
|---|---|---|
| JP | 4-337446 A | 11/1992 |
| JP | 2002-507762 A | 3/2002 |
| JP | 2002-543414 A | 12/2002 |
| JP | 2004-506192 A | 2/2004 |
| JP | 2005-098876 A | 4/2005 |
| JP | 2005-099662 A | 4/2005 |
| JP | 2005-164560 A1 | 6/2005 |
| JP | 2007-020565 A | 2/2007 |
| JP | 4023523 B2 | 12/2007 |
| JP | 2008-116440 A | 5/2008 |
| JP | 2008-536093 A | 9/2008 |
| JP | 2008-292371 A | 12/2008 |
| JP | 2009-145242 A | 7/2009 |
| JP | 2009-281831 A | 12/2009 |
| JP | 2009-288161 A | 12/2009 |
| JP | 2011-002415 A | 1/2011 |
| RU | 2 223 504 C1 | 2/2004 |
| WO | 98/16814 A1 | 4/1998 |
| WO | 99/47963 A1 | 9/1999 |
| WO | 00/66985 A1 | 11/2000 |
| WO | 02/12864 A1 | 2/2002 |
| WO | 2006/084283 A2 | 8/2006 |
| WO | 2007010803 A1 | 1/2007 |
| WO | 2007147159 A2 | 12/2007 |
| WO | 2008/007580 A1 | 1/2008 |
| WO | 2008/080417 A1 | 7/2008 |
| WO | 2009/117033 A2 | 9/2009 |
| WO | 2011/108369 A1 | 9/2011 |
| WO | 2011/108370 A1 | 9/2011 |
| WO | 2011/108371 A1 | 9/2011 |
| WO | 2012050011 A1 | 4/2012 |
| WO | 2013/031309 A1 | 3/2013 |
| WO | 2013/031439 A1 | 3/2013 |

OTHER PUBLICATIONS

F.J. Meyer-Almes, "A new Method for Use in Molecular Diagnostics and High Throughput Pharmaceutical Screening based on Fluorescence Correlation Spectroscopy", Nanoparticle Immunoassays, R. Rigler, edit, Springer, Berlin, 2000, pp. 204-224. (cited in specification).

Noriko Kato et al., "A single molecule analyzer that enable new analysis of DNA and protein interactions", Gene Medicine, vol. 6, No. 2, 2002, pp. 271-277. (cited in specification).

P. Kask et al., "Two-Dimensional Fluorescence Intensity Distribution Analysis: Theory and Applications", Biophysical Journal, vol. 78, pp. 1703-1713, Apr. 2000, Cited in Specification.

Peet Kask et al., "Fluorescence-intensity distribution analysis and its application in biomolecular detection technology", PNAS, vol. 96, No. 24, Nov. 23, 1999, pp. 13756-13761. (cited in specification).

International Search Report of PCT/JP2011/072939, mailing date of Nov. 29, 2011.

Goodwin et al. "Rapid sizing of individual fluorescently stained DNA fragments by flow cytometry," Nucleic Acids Research, 1993, vol. 21, No. 4 pp. 803-806.

Keller et al. "Single-Molecule Fluorescence Analysis in Solution," Applied Spectroscopy, 1996, vol. 50, No. 7, pp. 12A-32A.

Lee et al. "Laser-Induced Fluorescence Detection of a Single Molecule in a Capillary," Analytical Chemistry, Dec. 1, 1994, vol. 66, No. 23, pp. 4142-4149.

Li et al. "Ultrasensitive Coincidence Fluorescence Detection of Single DNA Molecules," Analytical Chemistry, Apr. 1, 2003, vol. 75, No. 7, pp. 1664-1670.

Nie et al. "Probing Individual Molecules with Confocal Fluorescence Microscopy," Science, Nov. 11, 1994, vol. 266, pp. 1018-1021.

Tahari, "Fluorescence Correlation Spectroscopy: Ultrasensitive Detection in Clear and Turbid Media," University of Illinois, 2005, pp. 1-88, Jun. 2, 2014.

Wu et al. "Development and Preliminary Clinical Validation of a High Sensitivity Assay for Cardiac Troponin Using a Capillary Flow (Single Molecule) Fluorescence Detector," Clinical Chemistry, 2006, vol. 52, No. 11, pp. 2157-2159.

Itoh et al. "A New Method for Detection of Influenza Viruses by Single Particle-Recognition Based on the Principle of Fluorescence Correlation Spectroscopy," Chemistry and Biology, 2009, vol. 47, No. 12, pp. 823-830.

Carlsson K et al: "Three-dimensional microscopy using a confocal laser scanning microscope", Optics Letters, Optical Society of America, vol. 10, No. 2, Feb. 1985 pp. 53-55, XP007922413.

Chinese Office Action issued Feb. 7, 2013, issued in related Chinese application No. 201180011644.5 with translation.

Extended European search report dated Mar. 28, 2013, issued in related EP application No. 11750481.1.

Japanese Office Action (mailing date Dec. 18, 2012) issued in related JP application No. 2012-503060 with English translation.

International Search Report dated Mar. 29, 2011 issued in related PCT/JP2011/053481.

Written Opinion of International Searching Authority (PCT/ISA/237) issued in related PCT/JP2011/053481.

International Preliminary Report on Patentability (PCT/IPEA/409) issued in related PCT/JP2011/053481 with English translation.

Chinese Office Action Aug. 9, 2013 issued in related Chinese application No. 201180011640.7 with English translation.

International Search Report dated Mar. 29, 2011 issued in related PCT/JP2011/053482.

International Preliminary Report on Patentability (PCT/IPEA/409) issued in related PCT/JP2011/053482.

Written Opinion of International Searching Authority (PCT/ISA/237) issued in related PCT/JP2011/053482.

U.S. Office Action dated Jan. 3, 2014, issued in related U.S. Appl. No. 13/597,825.

Chinese Office Action issued Aug. 13, 2013, issued in related Chinese application No. 201180011655.3 with English translation.

International Search Report dated Mar. 29, 2011, issued in related PCT/JP2011/053483.

(56) References Cited

OTHER PUBLICATIONS

International Preliminary Report on Patentability (PCT/IPEA/409) issued in related PCT/JP2011/053483.

Written Opinion of International Searching Authority (PCT/ISA/237) issued in related PCT/JP2011/053483.

U.S. Office Action dated Apr. 2, 2013, issued in co-pending U.S. Appl. No. 13/596,280.

Park et al, "Counting the Number of Fluorophores Labeled in Biomolecules by Observing the Fluorescence-Intensity Transient of a Single Molecule", Bulletin of the Chemical Society of Japan, dated Aug. 30, 2005, vol. 78, No. 9, (p. 1612-1618).

International Search Report dated Nov. 27, 2012, issued in related PCT/JP2012/077986.

U.S. Office Action mailed Sep. 16, 2013, issued in related U.S. Appl. No. 13/862,021.

U.S. Office Action mailed Oct. 4, 2013, issued in related U.S. Appl. No. 13/596,243.

Hebert, B et al. "Spatiotemporal Image Correlation Spectroscopy (STICS) Theory, Verification, and Application to Protein Velocity Mapping in Living CHO Cells", Biophysical Journal vol. 88, May 2005 pp. 3601-3614.

Supplemental European Search Report of Jun. 17, 2013 issued in corresponding EP application 11832447.

Nagai Takeharu et al., "How to Measure Diffusion Coefficient of Biomolecules in Living Cells", Biophysics vol. 49, No. 4, 2009, pp. 181-186.

Kinjo Masataka et al., "Analysis of DNA structure by measurement of diffusion rate", Japanese Society of Biorheology, vol. 9, No. 2, 1995, pp. 74-83.

International Search Report of PCT/JP2011/072898, mailing date of Nov. 29, 2011.

Machan Radek et al., "Recent Developments in Fluorescence Correlation Spectroscopy for Diffusion Measurements in Planar Lipid Membranes", International Journal of Molecular Sciences, 2010, pp. 427-457, ISSN 1422-0067.

Rigler. R et al. "Fluorescence correlation spectroscopy with high count rate and low background: analysis of translational diffusion", European Biophysics Journal, 1993, pp. 169-175.

\* cited by examiner

FIG. 1A
FIG. 1B
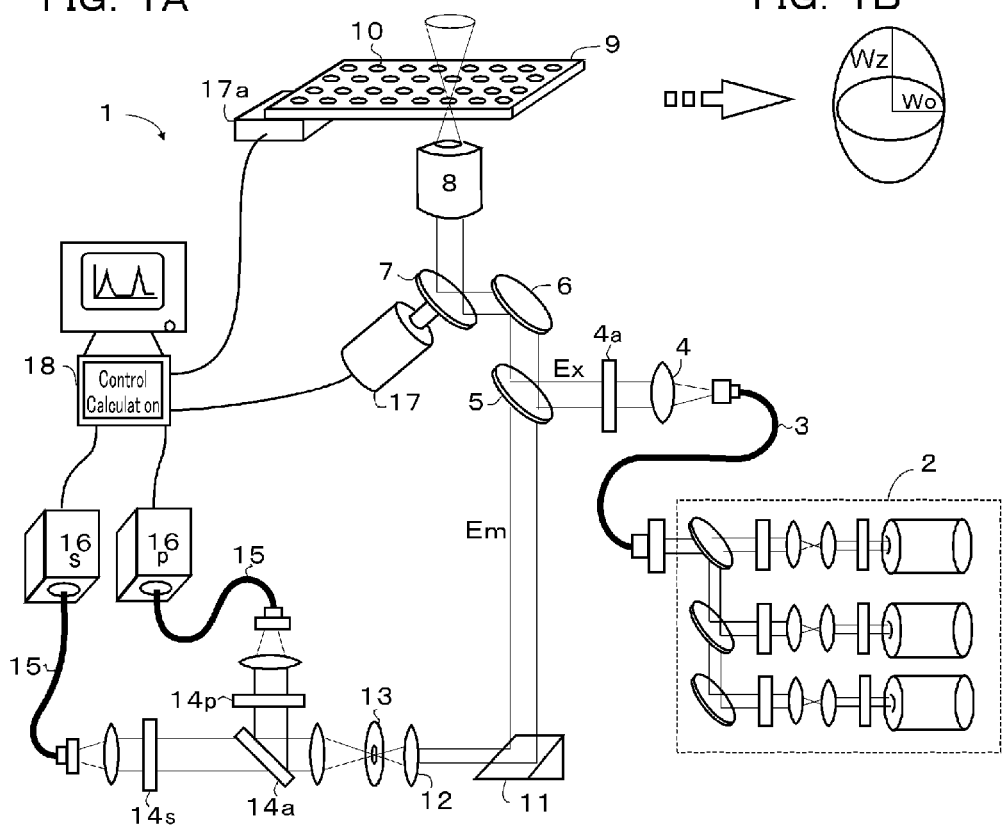
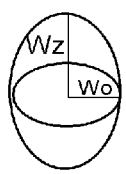
FIG. 1C
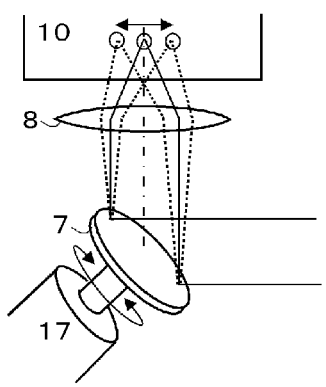

$$P = \frac{I_p - I_s}{I_p + I_s}$$

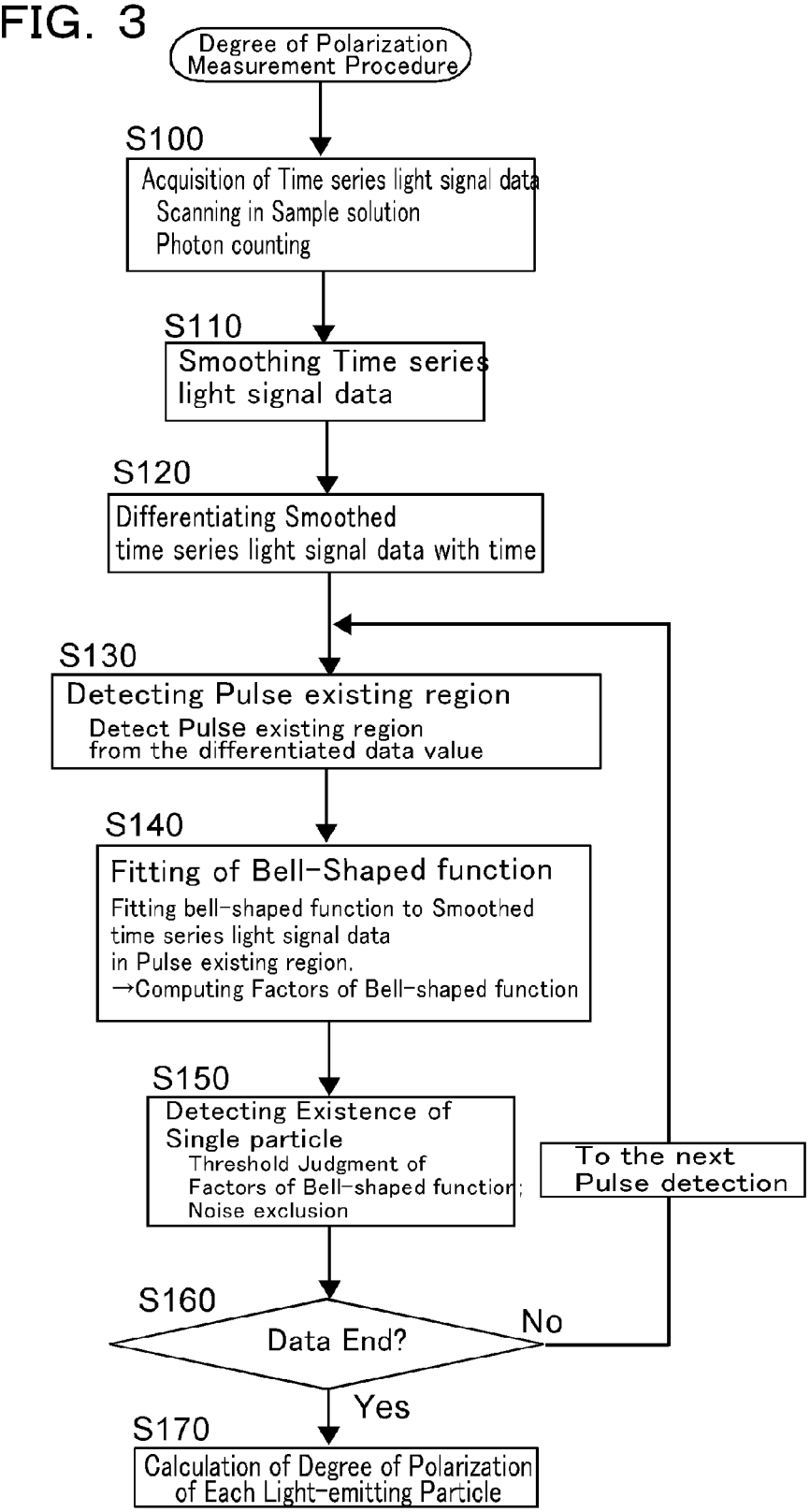

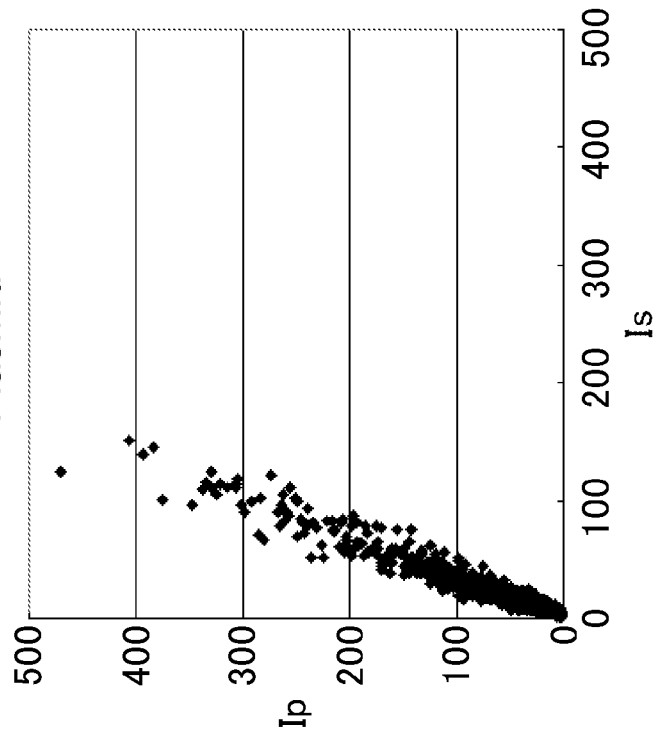
FIG. 6A TAMRA
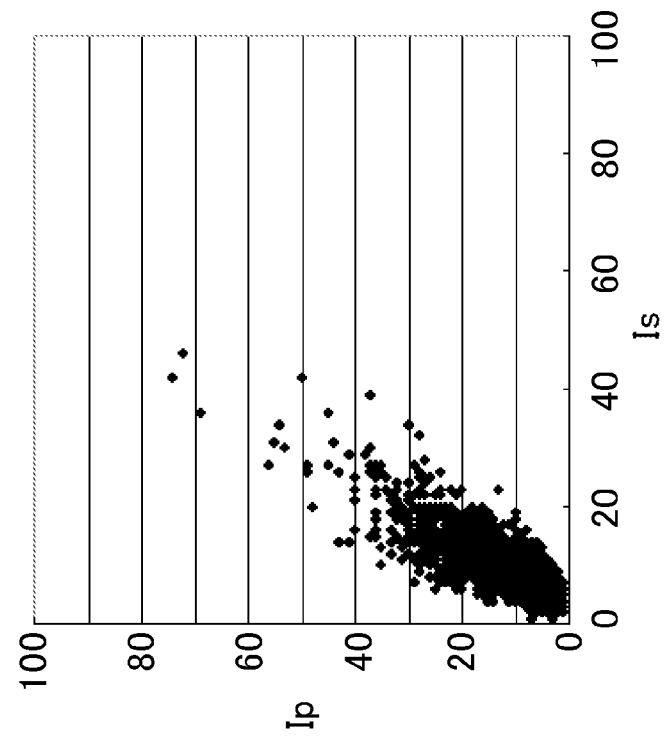
FIG. 6B Plasmid

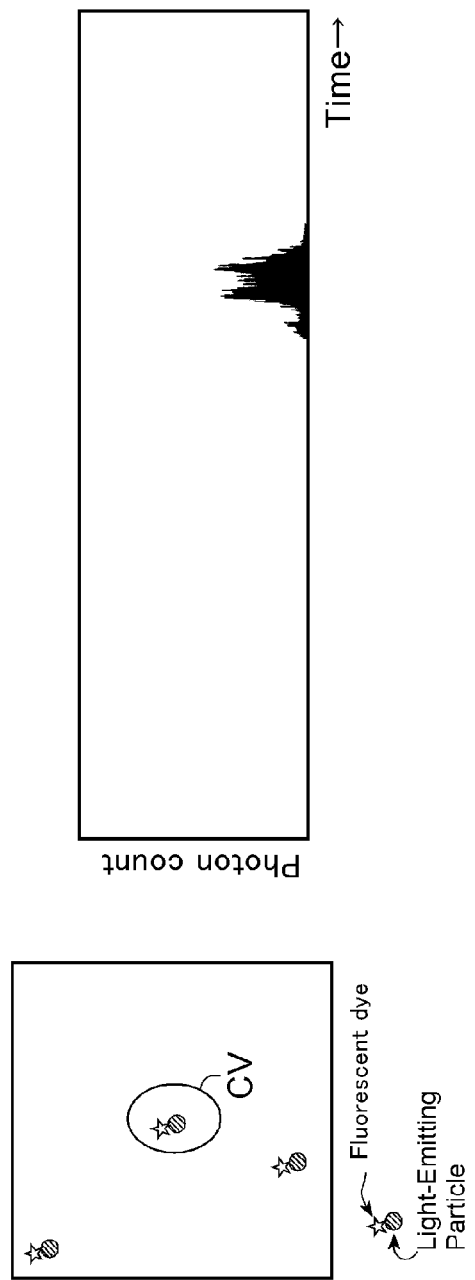
FIG. 7A High Concentration (e.g. ~ 1nM)
FIG. 7B Low Concentration (e.g. ~ 1pM)

OPTICAL ANALYSIS DEVICE, OPTICAL ANALYSIS METHOD AND COMPUTER PROGRAM FOR OPTICAL ANALYSIS FOR OBSERVING POLARIZATION CHARACTERISTICS OF A SINGLE LIGHT-EMITTING PARTICLE

TECHNICAL FIELD

This invention relates to an optical analysis device, an optical analysis method and a computer program for optical analysis capable of detecting light from a particulate object, e.g. an atom, a molecule or an aggregate thereof (Hereafter, these are called a "particle"), such as a biological molecule, for example, protein, peptide, nucleic acid, lipid, sugar chain, amino acid or these aggregate, virus and cell, etc., or a non-biological particle, dispersed or dissolved in a solution, by using an optical system, such as the optical system of a confocal microscope or a multiphoton microscope, which can detect light from a micro region in a solution, to acquire useful information in an analysis of conditions (interaction, binding or dissociating condition, etc.) of particles, and more specifically, relates to a technique of detecting the light from a single particle which emits light individually, using an optical system as described above, to make it possible to conduct various optical analyses. In this regard, in this specification, a particle which emits light (hereafter, referred to as a "light-emitting particle") may be any of a particle which itself emits light and a particle to which an arbitrary light-emitting label has been attached, and the light emitted from a light-emitting particle may be fluorescence, phosphorescence, etc. emitted with excitation light radiation.

BACKGROUND ART

According to the developments in optical measurement techniques in recent years, detection and/or measurement of faint light at a single photon or single fluorescent molecule level have become possible by using an optical system of a confocal microscope and a super high sensitive light detection technique capable of the photon counting (single photon detection). Thus, there are variously proposed devices or methods of performing detection of a characteristic, an inter-molecular interaction, a binding or dissociating reaction of a biological molecule, etc. by means of such a faint light measurement technique. For example, in Fluorescence Correlation Spectroscopy (FCS, see e.g. patent documents 1-3 and non-patent documents 1-3), by means of the optical system of a laser confocal microscope and a photon counting technique, there is performed the measurement of fluorescence intensity of fluorescent molecules or fluorescently labeled molecules (fluorescent molecules, etc.), entering into and exiting out of a micro region (the focal region to which the laser light of the microscope is condensed, called a "confocal volume") in a sample solution, and based on the average dwell time (translational diffusion time) of the fluorescent molecules, etc. and the average value of the number of the dwelling molecules in the micro region, determined from the autocorrelation function value of the measured fluorescence intensity, there are achieved the acquisition of information, such as the motion speed, the size or the concentration of the fluorescent molecules, etc., and/or the detection of various phenomena, such as a change of a molecular structure or size, a binding or dissociative reaction or dispersion and aggregation of molecules. Further, in Fluorescence Intensity Distribution Analysis (FIDA, e.g. patent document 4, non-patent document 4) or Photon Counting Histogram (PCH, e.g. patent document 5), there is generated a histogram of fluorescence intensity of fluorescent molecules, etc., entering into and exiting out of a confocal volume, measured similarly to FCS; and the average value of the characteristic brightness of the fluorescent molecules, etc. and the average number of molecules dwelling in the confocal volume are calculated by fitting a statistical model formula to the distribution of the histogram, so that, based on the information thereof, the structure or size changes, binding or dissociative conditions or dispersion and aggregation conditions of molecules can be estimated. Furthermore, in FIDA, by dividing detected fluorescence into polarized light components and analyzing in two channels, it has been also possible to obtain the polarization characteristics of a target molecule (Fluorescence Intensity Distribution Analysis—Polarization: FIDA-PO) (nonpatent document 5). In FIDA-PO, the intensity histograms of a p polarized light component (horizontal polarized light component) and an s polarized light component (vertical polarized light component) of the fluorescence are generated, respectively, and from the averages of the intensities of the respective polarized light components of the fluorescent molecules, etc. computed through the fitting of the statistical model formula to the distributions of those histograms, the polarization degree of the fluorescent molecules, etc. is computed. In addition, in patent documents 6 and 7, there are proposed methods of detecting fluorescent substances based on a time progress of fluorescence signals of a sample solution measured using the optical system of a confocal microscope. Patent document 8 has proposed a signal calculation processing technique for measuring faint light from fluorescent fine particles flowing through a flow cytometer or fluorescent fine particles fixed on a substrate by a photon counting technique to detect the existences of the fluorescent fine particles in the flow or on the substrate.

Especially, according to the methods employing the measurement technique of fluorescent light of a micro region using the optical system of a confocal microscope and a photon counting technique, such as FCS and FIDA, a sample amount required for the measurement may be extremely small (an amount used in one measurement is at most several tens of μL), and its concentration is extremely low as compared with the prior art, and the measuring time is also shortened extremely (In one measurement, a measuring process for time of order of seconds is repeated several times). Thus, those techniques are expected to be a strong tool enabling an experiment or a test at low cost and/or quickly in comparison with conventional biochemical methods, especially in conducting an analysis of a rare or expensive sample often used in the field of the medical or biological research and development or in conducting tests of a large number of specimens, such as sick clinical diagnosis or the screening of bioactive substances.

PRIOR TECHNICAL DOCUMENTS

Patent Documents

Patent document 1: Japanese Patent laid-open publication No. 2005-098876
Patent document 2: Japanese Patent laid-open publication No. 2008-292371
Patent document 3: Japanese Patent laid-open publication No. 2009-281831
Patent document 4: Japanese Patent No. 4023523
Patent document 5: WO 2008-080417
Patent document 6: Japanese Patent laid-open publication No. 2007-20565

Patent document 7: Japanese Patent laid-open publication No. 2008-116440
Patent document 8: Japanese Patent laid-open publication No. 4-337446

Non-Patent Documents

Non-patent document 1: Masataka Kaneshiro; "Protein, Nucleic acid, Enzyme" Vol. 44, No. 9, pages 1431-1438, 1999.
Non-patent document 2: F. J. Meyer-Alms; "Fluorescence Correlation Spectroscopy" edt. R. Rigler, Springer, Berlin, pages 204-224, 2000.
Non-patent document 3: Noriko Kato, et al. "Gene medicine", Vol. 6, No. 2, pages 271-277.
Non-patent document 4: P. Kask, K. Palo, D. Ullmann, K. Gall PNAS 96, 13756-13761 (1999)
Non-patent document 5: P. Kask, K. Palo, N. Fay, L. Brand, U. Mets, D. Ullmann, and J. Jungmann: Biophys. J. 78, 1703 (2000)

SUMMARY OF INVENTION

Technical Problem

In the above-mentioned optical analysis technique using the optical system of a confocal microscope and a photon counting technique, such as FCS, and FIDA, although the measured light is the light emitted from single or several fluorescent molecules, there are conducted in the analysis of the light the statistical procedures for the calculating of the fluorescence intensity fluctuation, etc., such as the computation of the autocorrelation function or the fitting to the histogram of fluorescence intensity data measured in time series, and therefore the signal of the light from an individual fluorescent molecule is not seen or analyzed. That is, in these optical analysis techniques, through the statistical processing of the signals of the lights from a plurality of fluorescent molecules, etc., statistical average characteristics of the fluorescent molecules, etc. will be detected. Thus, in order to obtain a statistically significant result in these optical analysis techniques, the concentration or number density of a fluorescent molecule, etc. to be an observation object in the sample solution should be at a level so that fluorescent molecules, etc. of the number enabling a statistical process will enter in and exit from a micro region in one measuring term of a length of order of seconds in an equilibrium, preferably at a level so that about one fluorescent molecule, etc. will be always present in the micro region. Actually, since the volume of a confocal volume is about 1 fL, the concentration of a fluorescent molecule, etc. in a sample solution used in the above-mentioned optical analysis technique is typically at the level of 1 nM or more, and at much less than 1 nM, there is produced a term in which no fluorescent molecules, etc. are present in the confocal volume so that no statistically significant analysis result will be obtained. On the other hand, in the detection methods of fluorescent molecules, etc. described in patent documents 6-8, no statistical computation processes of fluorescence intensity fluctuation are included so that fluorescent molecules, etc. even at less than 1 nM in a sample solution can be detected, but, it has not been achieved to compute quantitatively the concentration or number density of a fluorescent molecule, etc. moving at random in a solution.

Then, in Japanese patent application No. 2010-044714 and PCT/JP2011/53481, Applicant of the present application has proposed an optical analysis technique based on a new principle which makes it possible to observe quantitatively a condition or characteristic of a light-emitting particle in a sample solution where the concentration or number density of the light-emitting particle to be an observation object is lower than the level at which the optical analysis techniques including statistical procedures, such as FCS and FIDA, etc. are used. In this new optical analysis technique, briefly, there is used an optical system which can detect light from a micro region in a solution, such as an optical system of a confocal microscope or a multiphoton microscope, similarly to FCS, FIDA, etc., and additionally, the position of the micro region, i.e. the detection region of light (called "light detection region" in the following) is moved in the sample solution, namely, the inside of the sample solution is scanned with the light detection region, and when the light detection region encompasses a light-emitting particle, dispersed and moving at random in the sample solution, the light emitted from the light-emitting particle is detected, and thereby each of the light-emitting particles in the sample solution is detected individually so that it becomes possible to perform the counting of light-emitting particles and the acquisition of the information about the concentration or number density of the light-emitting particle in the sample solution. According to this new optical analysis technique (called a "scanning molecule counting method", hereafter), not only a sample amount necessary for measurement may be small (for example, about several 10 μL) and the measuring time is short similarly to optical analysis techniques, such as FCS and FIDA, but also, it becomes possible to detect the presence of a light-emitting particle and to quantitatively detect its characteristic, such as a concentration, a number density, etc., at a lower concentration or number density, as compared with the case of optical analysis techniques, such as FCS and FIDA.

In order to further develop the new optical analysis technique proposed in the above-mentioned patent applications 2010-044714 and PCT/JP2011/53481, the main object of the present invention is especially to propose an optical analysis device, an optical analysis method and a computer program for optical analysis capable of measuring specific polarized light components of light in a measurement of the light from a light-emitting particle and analyzing the polarization characteristic of each light-emitting particle with the new optical analysis technique.

Solution to Problem

According to the present invention, the above-mentioned object is achieved by an optical analysis device which detects light from a light-emitting particle dispersed and moving at random in a sample solution using an optical system of a confocal microscope or a multiphoton microscope, comprising a light detection region moving portion which moves a position of a light detection region of the optical system of the microscope in the sample solution by changing an optical path of the optical system; a light irradiating portion which irradiates the light detection region with excitation light consisting of (a) predetermined polarized light component(s); a light detecting portion which detects an intensity of at least one polarized light component of light from the light detection region; and a signal processing portion which detects individually a signal from each light-emitting particle in the intensity of the at least one polarized light component of the light detected with the light detecting portion with moving the position of the light detection region in the sample solution, and computes, based on the intensity of the at least one polarized light component of the signal of the light of the detected light-emitting particle, a polarization characteristic value of the light-emitting particle. In this structure, "a light-emitting particle dispersed and moving at random in a sample solution" may be a particle, such as an atom, a molecule or an aggregate of these, which is dispersed or dissolved in a sample solution and emits light, and it may be an arbitrary particulate matter making the Brownian motion freely in a solution without being fixed on a substrate, etc. The light-emitting particle is typically a fluorescent particle, but may be other particles emitting light with radiation of excitation light (a phosphorescent particle, etc.). The "light detection region" of the optical system of the confocal microscope or multiphoton microscope is the micro region where light is detected in those microscopes, which region corresponds to the region to which excitation light is condensed when the excitation light is given from an objective (Especially in a confocal microscope, this region is determined in accordance with the spatial relationship of an objective and a pinhole). Further, the extraction of at least one polarized light component of light from the light detection region may be done by using a polarization beam splitter, a polarizing plate, etc. "Polarization characteristic value" may be an arbitrary index value indicating a polarization characteristic of a light-emitting particle, and typically, it is the degree of polarization, but it may also be other arbitrary values obtained based on the intensity of at least one polarized light component, e.g. the intensity of an s polarized light component or a p polarized light component, their intensity ratio, an anisotropy of fluorescence, or phosphorescence, etc. "excitation light consisting of (a) predetermined polarized light component(s)" is typically light polarized substantially in one direction, but there may be employed light containing polarized light components in two or more directions, non-polarized light, circularly polarized light or elliptically polarized light, depending upon an experimental condition and/or a characteristic of a light-emitting particle to be an object observed. Further, in the followings in this specification, "a signal" means "a signal expressing light from a light-emitting particle" unless noted otherwise.

In the above-mentioned inventive device, similarly to the scanning molecule counting method, in the basic structure, the irradiation of the excitation light and the measurement of light intensity are sequentially performed while the position of a light detection region is moved in a sample solution, namely, while the inside of the sample solution is scanned with the light detection region. Then, when the moving light detection region encompasses a randomly moving light-emitting particle, the light from the light-emitting particle is detected by the light detecting portion, and thereby, the existence of one particle will be detected. In this structure, in this invention, while excitation light consisting of (a) predetermined polarized light component(s) as excitation light is irradiated to the light detection region, the intensity of at least one polarized light component in the light from the light detection region is measured, and a polarization characteristic value of a light-emitting particle is computed from the measured intensity of the at least one polarized light component. According to this structure, when a light-emitting particle enters into the route of the light detection region, its polarization characteristic can be observed individually, and therefore, there is no need to conduct statistical procedure for calculation of the fluorescence intensity fluctuation in optical analysis techniques, such as FIDA-PO, and thus, it is advantageous in that a polarization characteristic of a light-emitting particle can be observed even when the light-emitting particle concentration in a sample solution is lower than the level necessary in FIDA-PO etc. to obtain a good measurement result.

In an embodiment, the at least one polarized light component of the light of a light-emitting particle detected with the above-mentioned device may be typically an s polarized light component and a p polarized light component, which can be obtained by dividing the light which comes from the light detection region with a polarization beam splitter etc., and the polarization characteristic value may be computed based on the intensity of the s polarized light component and the intensity of the p polarized light component (a signal of light of a light-emitting particle), which have been measured independently. Especially, the intensity of a signal used in the computation of a polarization characteristic value may be the peak value of the intensity of at least one polarized light component of the signal of the light of a light-emitting particle, the time integration value of the intensity of at least one polarized light component of the signal of the light of a light-emitting particle, or the time integration value of a bell shaped function which has been fit to the time change of the intensity of at least one polarized light component of the signal of the light of a light-emitting particle, etc. In this regard, when an s polarized light component and a p polarized light component of light coming from the light detection region are detected independently, the detection sensitivity of the s polarized light component and the detection sensitivity of the p polarized light component may differ from one another due to the transmittance or reflectance difference of each element in the optical system with the polarization directions and/or the sensitivity difference of light detecting devices (photodetectors) with the polarization directions. Thus, in one manner of the above-mentioned inventive device, when the light detection portion measures independently the intensity of the s polarized light component and the intensity of the p polarized light component in the light from the light detection region, the signal processing portion may be designed to compute the polarization characteristic value based on the detected value of the intensity of the s polarized light component and the detected value of the intensity of the p polarized light component of the signal of the light of a light-emitting particle, using a correcting value which corrects the difference between the detection sensitivity of the intensity of the s polarized light component and the detection sensitivity of the intensity of the p polarized light component. According to this manner, there will be obtained a polarization characteristic value in which the difference between the detection sensitivity of the intensity of the s polarized light component and the detection sensitivity of the intensity of the p polarized light component in the device has been corrected.

With respect to the moving of the position of the light detection region in the above-mentioned inventive structure, the moving speed of the position of the light detection region in the sample solution is appropriately changed based on the characteristic or the number density or concentration of the light-emitting particle in the sample solution. As understood in ones skilled in the art, the condition of detected light from the light-emitting particle may change in accordance with its characteristic, number density or concentration in the sample solution. Especially, when the moving speed of the light detection region becomes quick, the amount of light obtained from one light-emitting particle will be reduced, and therefore it is preferable that the moving speed of the light detection region can be changed appropriately so that the light from one light-emitting particle can be measured precisely or with sufficient sensitivity.

Furthermore, with respect to the moving the position of the light detection region as described above, the moving speed of the position of the light detection region in the sample solution is preferably set to be higher than the diffusional moving velocity of a light-emitting particle (the average moving speed of a particle owing to the Brownian motion). As explained above, in the inventive device, the light detection region detects the light emitted from a encompassed light-emitting particle, so that the light-emitting particle will be detected individually. However, when a light-emitting particle moves at random owing to the Brownian motion to move into and out of the light detection region multiple times, it is possible that the signal from one light-emitting particle (showing its existence) will be detected multiple times, and therefore it would become difficult to make the existence of one light-emitting particle associated with the detected signal. Then, as described above, the moving speed of the light detection region is set higher than the diffusional moving velocity of the light-emitting particle, and thereby it becomes possible to make one light-emitting particle correspond to one signal. In this regard, since the diffusional moving velocity differs depending upon light-emitting particles, it is preferable that the moving speed of the light detection region can be changed appropriately according to the characteristics of the light-emitting particle as described above.

The changing of the optical path of the optical system for moving the position of the light detection region may be done in an arbitrary way. For example, the position of the light detection region may be changed by changing the optical path using a galvanomirror employed in the laser scan type optical microscope. The movement route of the position of the light detection region may be set arbitrarily, for example, which is selectable from circular, elliptical, rectangular, straight and curvilinear ones. In this connection, in the present invention, since the position of the light detection region is moved by changing the optical path of an optical system, the movement of the light detection region is quick without substantial generation of mechanical vibration and hydrodynamic effect in the sample solution, and therefore, the measurement of light can be performed under a stable condition without dynamic action affecting the light-emitting particle in the sample solution (without artifact) (For example, when a flow is generated in the sample, not only making the flow velocity always uniform is difficult, but also the device structure would become complicated, and furthermore, not only the required sample amount is substantially increased, but also it is possible that light-emitting particles or other substances in a solution would deteriorate or be denaturalized by the hydrodynamic action of the flow). Further, since no structure for flowing a sample solution is required, the measurement and analysis can be conducted with a small amount of the sample solution (at the level of one to several tens of μL) similarly to FCS, etc.

Moreover, in an embodiment of the inventive optical analysis device, the signal processing portion may be designed to count the number of the signals of the light-emitting particle detected individually, thereby counting the number of the light-emitting particles detected during the moving of the light detection region. Then, it becomes possible to acquire the information on the number density or concentration of the light-emitting particle as well as the polarization characteristic value.

The distinctive process of the optical analysis technique of detecting light of each light-emitting particle with moving the position of the light detection region in a sample solution and computing a polarization characteristic value of the light-emitting particle in the above-mentioned inventive device is realizable with a general-purpose computer. Therefore, according to another aspect of the present invention, there is provided a computer readable storage device having a computer program product including programmed instructions for optical analysis for detecting light from a light-emitting particle dispersed and moving at random in a sample solution using an optical system of a confocal microscope or a multiphoton microscope, said programmed instructions causing a computer to perform steps of: changing an optical path of the optical system of the microscope to move a position of a light detection region of the optical system in the sample solution; irradiating the light detection region with excitation light consisting of (a) predetermined polarized light component(s); detecting an intensity of at least one polarized light component of light from the light detection region with moving the position of the light detection region in the sample solution; and detecting a signal from each light-emitting particle individually in the intensity of the at least one polarized light component of the detected light and computing, based on the intensity of the at least one polarized light component of the detected signal of the light of the light-emitting particle, a polarization characteristic value of the light-emitting particle. In the present application, "computer readable storage device" does not cover transitory propagating signal per se.

Also in this computer program, the polarization characteristic value may be an arbitrary index value indicating a polarization characteristic of a light-emitting particle, such as the degree of polarization, the intensity of an s polarized light component or a p polarized light component, those intensity ratio, an anisotropy of fluorescence or phosphorescence, etc. Further, in the procedure of detecting the intensity of at least one polarized light component of the light from the light detection region, the intensities of the s polarized light component and the p polarized light component in the light from the light detection region may be measured separately, and in the procedure of computing a polarization characteristic value of the light-emitting particle, the polarization characteristic value may be computed based on the intensity of the s polarized light component and the intensity of the p polarized light component of the signal of the light of the light-emitting particle. The intensity of the signal used in the computation of the polarization characteristic value may be the peak value of the intensity of the at least one polarized light component of the signal of the light of a light-emitting particle, the time integration value of the intensity of at least one polarized light component of the signal of the light of a light-emitting particle, or the time integration value of a bell shaped function which has been fit to the time change of the intensity of the at least one polarized light component of the signal of the light of a light-emitting particle, etc.; and when the intensity of the s polarized light component and the intensity of the p polarized light component in the light from the light detection region are measured independently in the procedure of detecting the intensity of at least one polarized light component of the light from the light detection region, the polarization characteristic value may be computed based on the detected value of the intensity of the s polarized light component and the detected value of the intensity of the p polarized light component of the signal of the light of the light-emitting particle using a correcting value which corrects a difference between the detection sensitivity of the intensity of the s polarized light component and the detection sensitivity of the intensity of p polarized light component in the procedure of computing a polarization characteristic value of the light-emitting particle. Furthermore, in the above-mentioned computer program, there may be comprised a procedure of counting the number of the individually detected light signals from the light-emitting particles to count the number of the light-emitting particles detected during the moving of the position of the light detection region and/or the procedure of determining the number density or concentration of the light-emitting particle in the sample solution based on the number of the detected light-emitting particles. Moreover, in the procedure of changing the optical path of the optical system in order to move the position of the light detection region, the position of the light detection region may be moved at a predetermined velocity or at a velocity quicker than the diffusion moving velocity of the light-emitting particle, and the moving speed of the position of the light detection region may be set based on a characteristic or the number density or concentration of the light-emitting particle in the sample solution.

Furthermore, according to the above-mentioned inventive device or computer program, there is realized a new optical analysis method of detecting the light of each light-emitting particle with moving the position of a light detection region in a sample solution, and computing a polarization characteristic value of the light-emitting particle. Therefore, according to the present invention, there is provided an optical analysis method of detecting light from a light-emitting particle dispersed and moving at random in a sample solution using an optical system of a confocal microscope or a multiphoton microscope, comprising steps of: moving a position of a light detection region of the optical system of the microscope in the sample solution by changing an optical path of the optical system; irradiating the light detection region with excitation light consisting of predetermined (a) polarized light component(s); detecting an intensity of at least one polarized light component of light from the light detection region with moving the position of the light detection region in the sample solution; and detecting a signal from each light-emitting particle individually in the intensity of the at least one polarized light component of the detected light and computing, based on the intensity of the at least one polarized light component of the detected signal of the light of the light-emitting particle, a polarization characteristic value of the light-emitting particle.

Also in the above-mentioned method, the extraction of the at least one polarized light component of the light from the light detection region may be achieved with a polarization beam splitter, and the polarization characteristic value may be an arbitrary index value indicating a polarization characteristic of a light-emitting particle, such as the degree of polarization, the intensity of an s polarized light component or a p polarized light component, those intensity ratio, an anisotropy of fluorescence or phosphorescence, etc. Further, in the step of detecting an intensity of at least one polarized light component of the light from the light detection region, the intensities of the s polarized light component and p polarized light component in the light from the light detection region may be measured separately, and in the step of computing a polarization characteristic value of a light-emitting particle, the polarization characteristic value may be computed based on the intensity of the s polarized light component and the intensity of the p polarized light component of the signal of the light of the light-emitting particle. The intensity of the signal used in the computation of the polarization characteristic value may be the peak value of the intensity of the at least one polarized light component of the signal of the light of a light-emitting particle, the time integration value of the intensity of at least one polarized light component of the signal of the light of a light-emitting particle, or the time integration value of a bell shaped function which has been fit to the time change of the intensity of the at least one polarized light component of the signal of the light of a light-emitting particle, etc.; and when the intensity of the s polarized light component and the intensity of the p polarized light component in the light from the light detection region are measured independently in the step of detecting an intensity of the at least one polarized light component of the light from the light detection region, the polarization characteristic value may be computed based on the detected value of the intensity of the s polarized light component and the detected value of the intensity of the p polarized light component of the signal of the light of the light-emitting particle using a correcting value which corrects a difference between the detection sensitivity of the intensity of the s polarized light component and the detection sensitivity of the intensity of the p polarized light component in the step of computing a polarization characteristic value of the light-emitting particle. Furthermore, also in the above-mentioned method, there may be comprised a step of counting the number of the individually detected light signals from the light-emitting particles to count the number of the light-emitting particles detected during the moving of the position of the light detection region and/or the step of determining the number density or concentration of the light-emitting particle in the sample solution based on the number of the detected light-emitting particles. Moreover, in the step of changing the optical path of the optical system in order to move the position of the light detection region, the position of the light detection region may be moved at a predetermined velocity or at a velocity quicker than the diffusion moving velocity of the light-emitting particle, and the moving speed of the position of the light detection region may be set based on a characteristic or the number density or concentration of the light-emitting particle in the sample solution.

The optical analysis technique for observing a polarization characteristic of a light-emitting particle in accordance with the present invention is used, typically, for an analysis of a condition in a solution of a biological particulate object, such as a biological molecule, e.g. a protein, a peptide, a nucleic acid, a lipid, a sugar chain, an amino acid or these aggregate, a virus and a cell, etc., but it may be used for an analysis of a condition in a solution of a non-biological particle (for example, an atom, a molecule, a micelle, a metallic colloid, etc.), and it should be understood that such a case belongs to the scope of the present invention also.

Effect of Invention

Generally, according to the present invention, by scanning the inside of a sample solution with a light detection region in a confocal microscope or a multiphoton microscope, together with individual detection of an existence of a light-emitting particle, it becomes possible to observe a polarization characteristic of a light-emitting particle. And since a polarization characteristic of a light-emitting particle is a value reflecting the structure, size and shape of the particle, the observation according to the present invention enables the identification of a particle, the detection of the structure, size, shape and their change of a particle, or the detection and analysis of various phenomena, such as binding and dissociating reactions, dispersion and aggregation of particles.

The observation of a polarization characteristic in the above-mentioned present invention is based on a new principle, having the feature different from FIDA-PO. In FIDA-PO, the light of two or more light-emitting particles dispersed and moving at random in a sample solution is measured for each polarized light component; the intensity histogram is generated; the average of the intensity for each polarized light component is computed by fitting a theoretical formula to the histogram; and then, a polarization characteristic value is computed. Thus, in the presences of light-emitting particles of different kinds in a sample solution, the calculating process becomes complicated, and thus, for instance, when a measurement by FIDA-PO for a particle is performed through the attaching of a light-emitting probe to the particle to be an observation object, the purification treatment for removing light-emitting probes having not bound to a particle to be detected may be needed. Furthermore, as already noted, in order to calculate the average of fluorescence intensity in good precision by FIDA-PO, the light-emitting particle concentration in a sample solution should be at a level at which one or more light-emitting particle(s) always exist(s) during the measuring time. On the other hand, according to the present invention, it is possible to compute a polarization characteristic value by detecting individually the polarized light component(s) of a light-emitting particle. Accordingly, the light-emitting particle concentration in a sample solution at which the measurement can be performed in good accuracy will be significantly lower than in the case of FIDA-PO, and when a kind of light-emitting particle can be discriminated with a signal characteristic, etc., whether or not light-emitting particles of different kinds are present in a sample solution seldom influences the difficulty in calculation of a polarization characteristic value, and therefore, also in measuring for a particle to which a light-emitting probe was attached, advantageously, the removal of light-emitting probes becomes unnecessary. Moreover, since a light-emitting particle is detected individually in the present invention, even a light-emitting particle, whose concentration is relatively low in a sample solution so that its light can be buried in the light from other light-emitting particles in a conventional method, is detectable and its polarization characteristic is observable.

Other purposes and advantages of the present inventions will become clear by explanations of the following preferable embodiments of the present invention.

BRIEF DESCRIPTIONS OF DRAWINGS

FIG. 1A is a schematic diagram of the internal structure of an optical analysis device realizing the present invention. FIG. 1B is a schematic diagram of a confocal volume (an observation region of a confocal microscope). FIG. 1C is a schematic diagram of the mechanism for changing the direction of the mirror 7 to move the position of a light detection region in a sample solution.

Figure 2B:
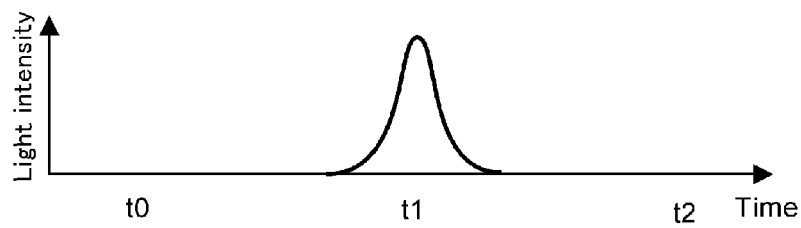
Figure 2C:
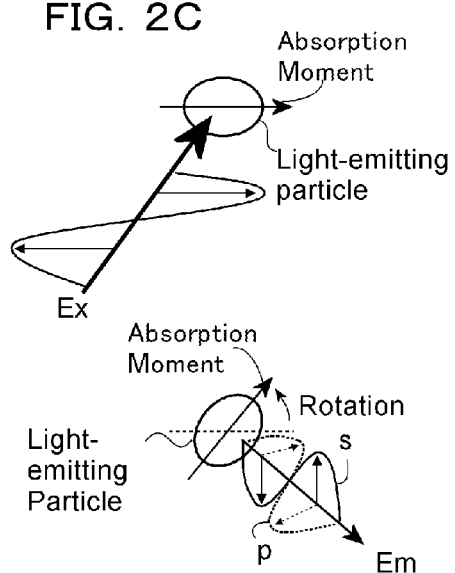
Figure 2D:
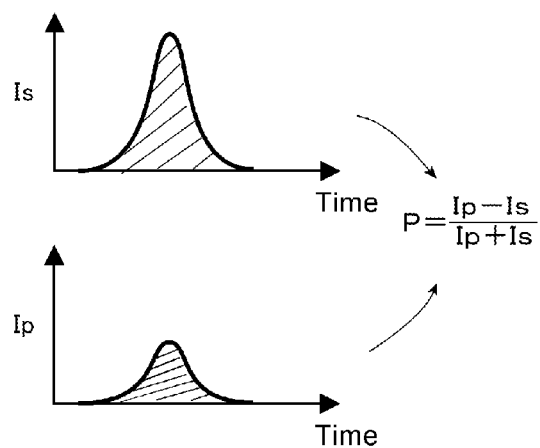

FIGS. 2A and 2B are a schematic diagram explaining the principle of the light detection and a schematic diagram of the variation of the measured light intensity with time in the scanning molecule counting method which constitutes a part of the present invention, respectively. FIG. 2C is a drawing of a model showing schematically polarized light components emitted from a light-emitting particle, and FIG. 2D is a schematic diagram of the time change of the light intensity of each polarized light component.

FIG. 3 is a drawing showing in the form of a flow chart the processes of the measurement of a diffusion constant to be performed according to the present invention.

Figure 4A:
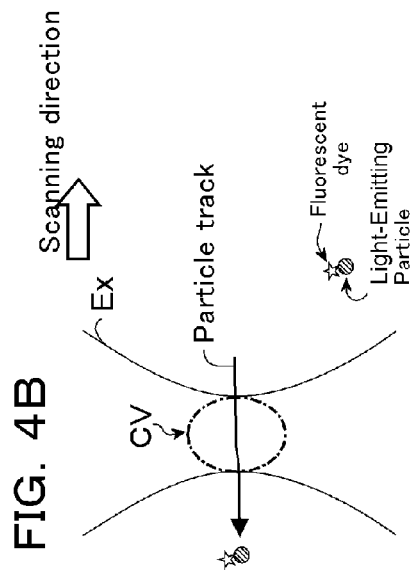
Figure 4B:
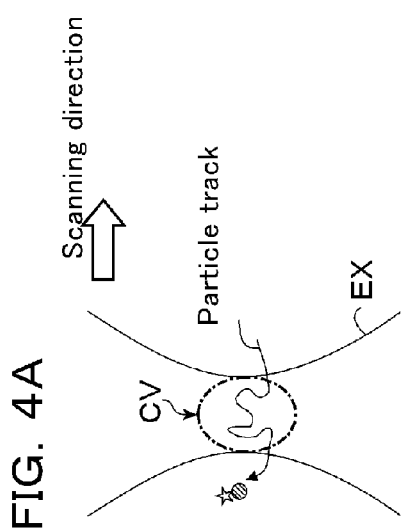
Figure 4C:
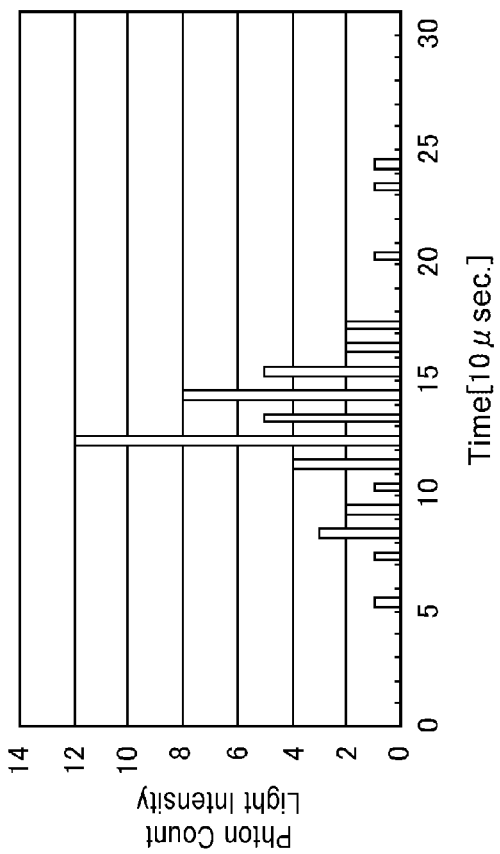

FIGS. 4A and 4B each are drawings of models in a case that a light-emitting particle crosses a light detection region owing to the Brownian motion and in a case that a light-emitting particle crosses a light detection region by moving the position of the light detection region in a sample solution at a velocity quicker than the diffusional moving velocity of the light-emitting particle, and FIG. 4C shows an example of a time change of a signal indicating light (photon count) from one light-emitting particle when the moving speed of the light detection region is set as in FIG. 4B.

Figure 5A:
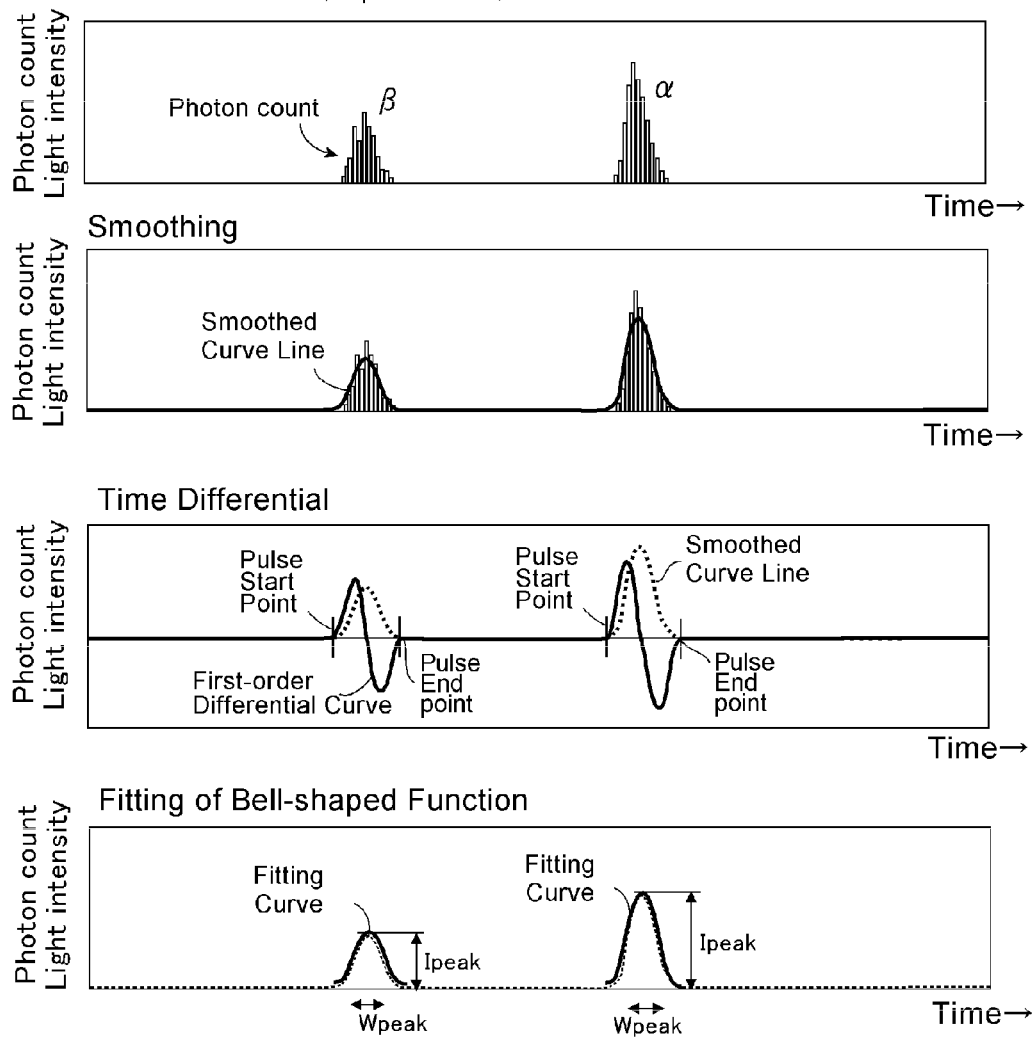
Figure 5B:
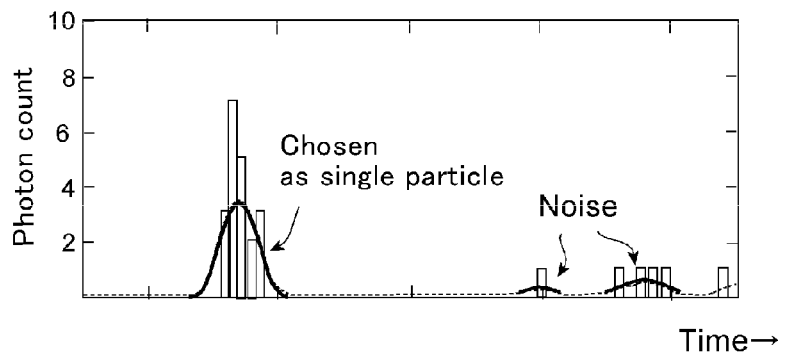

FIG. 5A shows drawings explaining an example of the signal processing step of the detected signals in the procedure for detecting the existence of a light-emitting particle from the measured time series light intensity data (change in time of photon count) in accordance with the scanning molecule counting method. FIG. 5B shows examples of measured photon count data (bar graph); curves obtained by carrying out the smoothing of the data (dotted line); and Gauss functions fitted on the pulse existing regions (solid line). In the drawing, the signals attached with "noise" are disregarded as signals due to noises or contaminants.

FIG. 6 is a diagram in which the p polarized component intensities Ip of the respective light-emitting particles detected according to the invention are plotted against the s polarized component intensities Is of the corresponding light-emitting particles. FIG. 6A is a case where TAMRA was used as a light-emitting particle, and FIG. 6B is a case where a plasmid stained with SYTOX Orange was used as a light-emitting particle.

FIG. 7 show examples of the time variation of the photon count (light intensity) obtained in a conventional optical analysis technique computing fluorescence intensity fluctuation, where FIG. 7A shows a case that the particle concentration is at a level providing a sufficient precision in the measurement, and FIG. 7B shows a case that the particle concentration in a sample is significantly lower than the case of FIG. 7A.

EXPLANATIONS OF REFERENCE NUMERALS

1—Optical analysis device (confocal microscope)
2—Light source
3—Single mode optical fiber
4—Collimating lens
4a—Excitation light polarizing element
5—Dichroic mirror
6, 7, 11—Reflective mirror
8—Objective
9—Micro plate
10—Well (sample solution container)
12—Condenser lens
13—Pinhole
14a—Polarization beam splitter
14s, p—Barrier filter
15—Multi-mode optical fiber
16s, p—Photodetector
17—Mirror deflector
17a—Stage position changing apparatus
18—Computer

DESCRIPTION OF EMBODIMENTS

In the followings, preferable embodiments of the present invention are described in detail.

Structure of Optical Analysis Device

In the basic structure, the optical analysis technique according to the present invention can be realized with an optical analysis device constructed by associating the optical system of a confocal microscope and photodetectors, enabling FIDA-PO, as schematically illustrated in FIG. 1A. Referring to FIG. 1A, the optical analysis device 1 consists of an optical system 2-17 and a computer 18 for acquiring and analyzing data together with controlling the operation of each part in the optical system. The optical system of the optical analysis device 1 may be the same as the optical system of a usual confocal microscope, where laser light emitted from a light source 2 and transmitted through the inside of a single mode fiber 3 (Ex) forms light diverging to be radiated at the angle decided by an inherent NA at the emitting end of the fiber; and after forming a parallel beam with a collimator 4, the light is adjusted to be the light in a predetermined polarization direction in the polarizing element 4a (through which typically either one of the p polarized light or s polarized light penetrates) and then reflected on a dichroic mirror 5 and reflective mirrors 6 and 7, entering into an objective 8. Above the objective 8, typically, there is placed a sample container or a micro plate 9 having wells 10 arranged thereon, to which one to several tens of μL of a sample solution is dispensed, and the laser light emitted from the objective 8 is focused in the sample solution in the sample container or well 10, forming a region having strong light intensity (excitation region). In the sample solution, light-emitting particles to be observed objects, which are typically molecules to which a light emitting label such as a fluorescent dye is attached, are dispersed or dissolved, and when a light-emitting particle enters into the excitation region, the light-emitting particle is excited and emits light during dwelling in the excitation region. The emitted light (Em), after passing through the objective 8 and the dichroic mirror 5, is reflected on the mirror 11 and condensed by a condenser lens 12, and then the light passes through the pinhole 13. In this regard, as known in ones skilled in the art, the pinhole 13 is located at a conjugate position of the focal position of the objective 8, and thereby only the light emitted from the focal region of the laser light, i.e., the excitation region, as schematically shown in FIG. 1B, passes through the pinhole 13 while the light from regions other than the focal plane is blocked. The focal region of the laser light illustrated in FIG. 1B is a light detection region, whose effective volume is usually about 1-10 fL, in this optical analysis device, which is called as a "confocal volume". In the confocal volume, typically, the light intensity is spread in accordance with a Gaussian type or Lorentz type distribution having the peak at the center of the region, and the effective volume is a volume of an approximate ellipsoid bordering a surface where the light intensity reduced to $1/e^2$ of the peak intensity. Then, the light having passed through the pinhole 13 is divided into the s polarized light component and p polarized light component with a polarization beam splitter 14a, and each of these passes through the corresponding barrier filter 14s, 14p (where a light component only in a specific wavelength band is selected); and is introduced into a multimode fiber 15, reaching to the corresponding photodetector 16s, 16p. In the photodetectors 16s, 16p, the respective sequentially coming lights are converted into time series electric signals, and the signals are inputted into the computer 18, where the processes for optical analysis are executed in a manner explained later. For the photodetectors 16s, 16p, preferably, super high sensitive photodetectors, usable for the photon counting, are used, so that the light from one light-emitting particle, for example, the faint light from one or several fluorescent dye molecule(s), can be detected. Thus, with the above-mentioned structure, the light intensity from a light-emitting particle is measured separately by the polarization direction.

Furthermore, in the optical system of the above-mentioned optical analysis device, there is further provided a mechanism for changing the optical path of the optical system to scan the inside of the sample solution with the light detection region, namely to move the position of the focal region i.e., the light detection region, within the sample solution. For this mechanism for moving the position of the light detection region, for example, there may be employed a mirror deflector 17 which changes the direction of the reflective mirror 7, as schematically illustrated in FIG. 1C. This mirror deflector 17 may be the same as that of a galvanomirror device equipped on a usual laser scan type microscope. Also, in order to attain a desired moving pattern of the position of the light detection region, the mirror deflector 17 is driven in harmony with the light detection of the photodetectors 16s, p under the control of the computer 18. The movement route of the position of the light detection region may be arbitrarily selected from circular, elliptical, rectangular, straight and curvilinear ones, or a combination of these (The program in the computer 18 may be designed so that various moving patterns can be selected). In this regard, although not illustrated, the position of the light detection region may be moved in the vertical direction by moving the objective 8 up and down. As noted, according to the structure of changing the optical path of the optical system to move the position of the light detection region instead of moving the sample solution, neither mechanical vibration nor hydrodynamic action occur substantially in the sample solution, so that it becomes possible to eliminate the influence of a dynamic action on an object to be observed, achieving the stable measurement.

Also, for an additional structure, on the stage (not shown) of the microscope, there may be provided a stage position changing apparatus 17a for moving the horizontal position of the micro plate 9, in order to change the well 10 to be observed. The operation of the stage position changing apparatus 17a may be controlled by the computer 18.

In the case that a light-emitting particle emits light by multiple photon absorption, the above-mentioned optical system is used as a multiphoton microscope. In that case, since the light is emitted only from the focal region of the excitation light (light detection region), the pinhole 13 may be removed. When a light-emitting particle emits light owing to phosphorescence, the above-mentioned optical system of the confocal microscope is used as it is. Furthermore, in the optical analysis device 1, as shown in the drawing, two or more excitation light sources 2 may be provided so that the wavelength of the excitation light can be appropriately selected in accordance with the wavelength of the light for exciting a light-emitting particle.

Principle of the Present Invention

As described in the column of "Summary of Invention", according to the inventive optical analysis technique, briefly, in the "scanning molecule counting method" which detects an existence of a light-emitting particle dispersed in a sample solution individually by detecting the light emitted when the light-emitting particle is encompassed in a light detection region of a confocal microscope or a multiphoton microscope within the sample solution with moving the position of the light detection region, at least one polarized light component of the light of the light-emitting particle is measured, and a polarization characteristic of the light-emitting particle is determined. According to this structure, each of the light-emitting particles in the sample solution will be detected individually, and its polarization characteristic will be observed, and therefore, the measurement of a polarization characteristic of a light-emitting particle becomes possible even when the light-emitting particle concentration in the sample solution is lower than the concentration well measurable by FIDA-PO which requires the statistical procedure for calculation of the magnitude of fluorescence fluctuation. In the following, the principle of measurement of the polarization characteristic in accordance with the present invention will be explained.

1. Principle of Scanning Molecule Counting Method

Spectral analysis techniques, such as FIDA, etc., are advantageous in that the required sample amount is extremely small and a test can be performed promptly as compared with the conventional biochemical analytical techniques. However, in these spectral analysis techniques such as FIDA, etc., the concentration and characteristics of a light-emitting particle are principally computed based on the fluorescence intensity fluctuation, and therefore, in order to obtain accurate measurement results, the concentration or number density of the light-emitting particle in a sample solution should be at the level where about one light-emitting particle always exists in a light detection region CV during the fluorescence intensity measurement as schematically drawn in FIG. 7A so that significant light intensity (photon count) can be always detected in the measuring term as shown in the right-hand side of the drawing. When the concentration or number density of the light-emitting particle is lower than that, for example, at the level where the light-emitting particle rarely enters into the light detection region CV as drawn on FIG. 7B, no significant light intensity signal (photon count) would appear in a part of the measuring term as illustrated on the right-hand side of the drawing, and thus, accurate computation of light intensity fluctuation would become difficult. Also, when the concentration of the light-emitting particle is significantly lower than the level where about one light-emitting particle always exists in the inside of the light detection region during the measurement, the calculation of light intensity fluctuation would become subject to the influence of the background, and also, the measuring term should be made long in order to obtain the significant quantity of the light intensity data (photon count) sufficient for the calculation.

Then, in the Japanese patent application no. 2010-044714, and PCT/JP2011/53481, the applicant of the present application has proposed "Scanning molecule counting method" based on a new principle which enables the detection of characteristics of a light-emitting particle, even when the concentration of the light-emitting particle is lower than the level requested in the above-mentioned spectral analysis techniques, such as FCS and FIDA.

In the scanning molecule counting method, briefly speaking, as the processes to be performed, the light detection is performed together with moving the position of the light detection region CV in a sample solution, namely, scanning the inside of the sample solution with the light detection region CV by driving the mechanism (mirror deflector 17) for moving the position of the light detection region to change the optical path as schematically drawn in FIG. 1C. Then, for example, as in FIG. 2A, during the moving of the light detection region CV (in the drawing, time t0-t2), when the light detection region CV passes through a region where one light-emitting particle exists (t1), light is emitted from the light-emitting particle, and a pulse form signal having significant light intensity (Em) appears on time series light intensity data as drawn in FIG. 2B. Thus, by detecting, one by one, each pulse form signal (significant light intensity) appearing as illustrated in FIG. 2B during the execution of the moving of the position of the light detection region CV and the light detection as described above, the light-emitting particles are detected individually, and the characteristic of the light-emitting particle existing in the measured region can be acquired. In the principle of the scanning molecule counting method, no statistical calculation processes, such as the calculation of the fluorescence intensity fluctuation, are conducted and the light-emitting particles are one by one detected, and therefore, the information about the characteristic of the particle is acquirable even in a sample solution with a low particle concentration at the level where no sufficiently accurate analysis is available in FCS, FIDA, etc.

2. Principle of a Polarization Characteristic of a Light-Emitting Particle According to the Present Invention In the present invention, especially in the above-mentioned scanning molecule counting method, as explained in conjunction with FIG. 1, by dividing the light from a light-emitting particle into polarized light components and measuring the intensities of the polarized light components independently, the polarization characteristic of the light-emitting particle is detected. In the detection of the polarization characteristic, typically, as schematically drawn in FIG. 2C, the light polarized in a certain direction is given to a light-emitting particle as excitation light Ex, and the s polarized light component and p polarized light component of light emitted from the light-emitting particle each are detected separately. And, by using the intensities of the respective detected polarized light components, for example, the integration value of a signal (the area value of the shaded region in FIG. 2D) or the peak intensity (the maximum) of a signal, an index value indicating a polarization characteristic, for example, a degree of polarization P, is computed. In the light Em emitted from a light-emitting particle having absorbed the excitation light Ex, its polarization direction is different from that of the excitation light Ex owing to various factors, for example, the autorotation of the particle by the rotatory Brownian motion, energy transfer, etc., and thus, from the index value indicating the polarization characteristic, information about the speed of the rotatory Brownian motion of the light-emitting particle, the presence or absence of energy transfer, etc. will be acquired, and further, from those information, there will be acquired information about the size and/or structure of the particle, an intermolecular interaction (binding and maceration), etc. Especially, it should be understood that, since the light from a single light-emitting particle passing through the light detection region is measured in the scanning molecule counting method, it is also possible to compute the polarization characteristic value of a single light-emitting particle individually. Thus, even in use of a sample solution of a light-emitting particle concentration lower than the concentration to be required for obtaining a good statistical calculation result in FIDA-PO, a polarization characteristic value becomes acquirable, and thereby information about the size and/or structure of a particle, intermolecular interaction, etc. will be acquired.

In this connection, how a polarized light component included in the light given as the excitation light is selected, and how polarized light components to be detected as detected lights are selected may be arbitrarily determined. The example in the explanation in conjunction with the above-mentioned device of FIG. 1A or FIG. 2C is so designed that a component polarized in one direction, for example, the p polarized light component, is radiated to the light detection region as the excitation light, and the p polarized light component and s polarized light component, divided from the light from the light detection region, are detected. However, for instance, non-polarized light may be given as the excitation light and either one of the s polarized light and p polarized light may be detected or both of the s polarized light and p polarized light may be detected separately. (In a case that, owing to a comparatively slow rotatory Brownian motion of a light-emitting particle, there occurs no change in the direction of a light-emitting particle or its change is detectable in one signal of the light-emitting particle, it becomes possible with the above-mentioned structure to observe the direction of the light-emitting particle or the speed of rotatory Brownian motion.) Further, the polarization setting of excitation light and the polarization setting of detected light may be selected in other various ways, and it should be understood that such a case belongs to the scope of the present invention.

Operation Processes

In the embodiment of the observation method of the polarization characteristic of a light-emitting particle in accordance with the present invention with the optical analysis device 1 as illustrated in FIG. 1A, concretely, there are conducted (1) a process of preparation of a sample solution containing light-emitting particles, (2) a process of measuring the light intensity of a sample solution and (3) a process of analyzing the measured light intensity. FIG. 3 shows the operation processes in this embodiment in the form of a flow chart.

(1) Preparation of a Sample Solution

The particle to be observed in the present invention may be an arbitrary particle as long as it is dispersed in a sample solution and moving at random in the solution, such as a dissolved molecule, and the particle may be, for instance, a biological molecule, i.e. a protein, a peptide, a nucleic acid, a lipid, a sugar chain, an amino acid, etc. or an aggregate thereof, a virus, a cell, a metallic colloid or other non-biological particle (Typically, the sample solution is an aqueous solution, but not limited to this, and it may be an organic solvent or other arbitrary liquids). Also, the particle to be observed may be a particle which emits light by itself, or may be a particle to which a light emitting label (a fluorescence molecule, a phosphorescence molecule) is attached in an arbitrary manner.

(2) Measurement of the Light Intensity of a Sample Solution

In the process of the measurement of the light intensity in accordance with the scanning molecule counting method of this embodiment, there is performed measuring the light intensity with driving the mirror deflector 17 to move the position of the light detection region within the sample solution (to scan in the sample solution) (FIG. 3—step 100). In the operation process, typically, after dispensing a sample solution into the well(s) 10 of the micro plate 9 and putting it on the stage of the microscope, when a user inputs to the computer 18 a command of a measurement start, the computer 18 executes programs (the process of changing the optical path in order to move the position of the light detection region in the sample solution, the process of irradiating the light detection region with excitation light and the process of detecting light from the light detection region during the moving of the position of the light detection region) memorized in a storage device (not shown), and then illuminating the light detection region in the sample solution with the excitation light and measuring light intensity will be started. When the measurement was started, under the control of the operation process of the computer 18 according to the programs, from the light source 2, the light of the excitation wavelength of a light-emitting particle in the sample solution is emitted, and the mirror deflector 17 drives the mirror 7 (galvanomirror) to move the position of the light detection region in the well 10, and simultaneously with this, the photodetectors 16s, p each convert sequentially the detected lights into electric signals and transmit them to the computer 18, which generates the time series light intensity data from the transmitted signals and store them in an arbitrary manner. The photodetectors 16s, p are typically super high sensitive photodetectors which can detect an arrival of a single photon, and thus the detection of light may be the photon counting performed in the manner of measuring sequentially the number of photons which arrive at the photodetector for every predetermined unit time (BIN TIME), for example, every 10 μs, during a predetermined time, and accordingly the time series light intensity data will be a time series photon count data.

Regarding the moving speed of the position of the light detection region, in order to perform quantitatively precisely individual detection of a light-emitting particle to be observed from the measured time series light intensity data in the scanning molecule counting method, preferably, the moving speed of the position of the light detection region during measurement of light intensity is set to a value quicker than the moving speed in the random motion, i.e., the Brownian motion of a light-emitting particle. When the moving speed of the position of the light detection region is slower than the movement of a particle owing to the Brownian motion, the particle moves at random in the region as schematically drawn in FIG. 4A, whereby the light intensity changes at random (the excitation light intensity in the light detection region is reduced from the peak at the center of the region toward its outside), so that it becomes difficult to determine a significant light intensity change corresponding to each light-emitting particle (a signal indicating light from a light-emitting particle). Then, preferably, as drawn in FIG. 4B, the moving speed of the position of the light detection region is set to be quicker than the average moving speed of a particle by the Brownian motion (diffusional moving velocity) so that the particle will cross the light detection region CV in an approximately straight line and thereby the profile of the change of the light intensity corresponding to each particle in the time series light intensity data becomes almost bell-shaped similarly to the excitation light intensity distribution as illustrated in the upper row of FIG. 4C and the correspondence between each light-emitting particle and light intensity can be easily determined.

Concretely, the time Δτ required for a light-emitting particle having a diffusion coefficient D to pass through the light detection region of radius r (confocal volume) by the Brownian motion is given from the expression of the relation of mean-square displacement:

$$(2r)^2 = 6D \cdot \Delta\tau \quad (1)$$

as:

$$\Delta\tau = (2r)^2/6D \quad (2),$$

and thus, the velocity of the light-emitting particle moving by the Brownian motion (diffusional moving velocity) Vdif, becomes approximately $$Vdif = 2r/\Delta\tau = 3D/r \quad (3)$$

Then, with reference to this, the moving speed of the position of the light detection region may be set to a value sufficiently quicker than Vdif. For example, when the diffusion coefficient of a light-emitting particle is expected to be about $D = 2.0 \times 10^{-10}$ m$^2$/s, Vdif will be $1.0 \times 10^{-3}$ m/s, supposing r is about 0.62 μm, and therefore, the moving speed of the position of the light detection region may be set to its 10 times or more, 15 mm/s. In this regard, when the diffusion coefficient of a light-emitting particle is unknown, an appropriate moving speed of the position of the light detection region may be determined by repeating the execution of a preliminary experiment with setting various moving speeds of the position of the light detection region in order to find the condition that the profile of a light intensity variation becomes an expected profile (typically, similar to the excitation light intensity distribution).

(3) Analysis of Light Intensity

When the time series light intensity data of a light-emitting particle in a sample solution are obtained by the above-mentioned processes, detection of a signal corresponding to light from a light-emitting particle on the light intensity data and calculation of a polarization characteristic value may be performed in the computer 18 through processes in accordance with programs memorized in a storage device.

(i) Detection of a Signal Corresponding to a Light-Emitting Particle

When the track of one light-emitting particle in its passing through the light detection region is approximately straight as shown in FIG. 4B, the light intensity variation in the signal corresponding to the particle to be observed in the time series light intensity data has a bell shaped profile reflecting the light intensity distribution in the light detection region (determined by the optical system) (see FIG. 4C). Thus, basically in the scanning molecule counting method, when the time width for which the light intensity exceeding an appropriately set threshold value continues is in a predetermined range, the signal having the profile of the light intensity may be judged to correspond to one particle having passed through the light detection region, and thereby one light-emitting particle is detected. And a signal whose time width for which the light intensity exceeding the threshold value continues is not in the predetermined range is judged as noise or a signal of a contaminant. Further, when the light intensity distribution in the light detection region can be assumed as Gaussian distribution:

$$I = A \cdot \exp(-2t^2/a^2) \quad (4),$$

and when the intensity A and the width a, computed by fitting Expression (4) to the profile of a significant light intensity (a profile which can be clearly judged not to be a background), are within the respective predetermined ranges, the profile of the light intensity may be judged to correspond to one particle having passed through the light detection region, and thereby the detection of one light-emitting particle will be done (The signal with the intensity A and the width a out of the predetermined ranges may be judged as a noise or a contaminant signal and ignored in the later analysis, etc.).

As an example of operational methods of conducting collective detection of light-emitting particles from time series light intensity, a smoothing treatment is performed to the time series light signal data (FIG. 5A, the upper row "detected result (unsettled)") (FIG. 3—step 110, FIG. 5A mid-upper row "smoothing"). Although the light emitted by a light-emitting particle is stochastic so that gaps will be generated in data values in minute time, such gaps in the data values can be disregarded by the smoothing treatment. The smoothing treatment may be done, for example, by the moving average method, etc. In this regard, parameters in performing the smoothing treatment, e.g., the number of datum points in one time of the averaging, the number of times of a moving average, etc. in the moving averages method, may be appropriately set in accordance with the moving speed (scanning speed) of the position of the light detection region and/or BIN TIME in the light intensity data acquisition.

Next, on the time series light intensity data after the smoothing treatment, in order to detect a time domain (pulse existing region) in which a significant pulse form signal (referred to as "pulse signal" hereafter) exists, the first differentiation value with time of the time series light intensity data after the smoothing treatment is computed (step 120). As illustrated in FIG. 5A, the mid-low row "time differential", in the time differential value of time series light signal data, the variation of the value increases at the time of the signal value change, and thereby, the start point and the end point of a significant signal can be determined advantageously by referring to the time differential value.

After that, a significant pulse signal is detected sequentially on the time series light intensity data, and it is judged whether or not the detected pulse signal is a signal corresponding to a light-emitting particle. Concretely, first, on the time series time-differential value data of the time series light intensity data, the start point and the end point of one pulse signal are searched and determined by referring to the time differential value sequentially, so that a pulse existing region will be specified (step 130). When one pulse existing region has been specified, the fitting of a bell-shaped function is applied to the smoothed time series light intensity data in the pulse existing region (FIG. 5A, the lower row "bell-shaped function fitting"), and then, parameters of the pulse of the bell-shaped function, such as the peak intensity (the maximum), Ipeak; the pulse width (full width at half maximum), Wpeak; the correlation coefficient in the fitting (of the least square method), etc. are computed (step 140). In this regard, although the bell-shaped function to be used in the fitting is typically a Gauss function, it may be a Lorentz type function. And it is judged whether or not the computed parameters of the bell-shaped function are within the respective ranges assumed for the parameters of the bell-shaped profile drawn by a pulse signal detected when one light-emitting particle passes a light detection region, i.e., whether or not each of the peak intensity, the pulse width and the correlation coefficient of the pulse is within the corresponding predetermined range (step 150). Then, the signal, whose computed parameters of the bell-shaped function are judged to be within the ranges assumed in a light signal corresponding to one light-emitting particle, as shown in FIG. 5B left, is judged as a signal corresponding to one light-emitting particle, and thereby, one light-emitting particle will be detected. On the other hand, a pulse signal, whose computed parameters of the bell-shaped function are not within the assumed ranges, as shown in FIG. 5B right, is disregarded as noise.

The search and judgment of a pulse signal in the processes of the above-mentioned steps 130-150 may be repetitively carried out in the whole region of the time series light signal data of each of the s polarized light component and p polarized light component (Step 160). Further, in the case of this embodiment, it is expected that the light of one light-emitting particle will appear in both of time series light intensity data of the s polarized light component and p polarized light component. Thus, one signal of each light-emitting particle is specified both in the time series light intensity data of the s polarized light component and p polarized light component. The associating of the signal on the time series light intensity data of the s polarized light component and the signal on the time series light intensity data of the p polarized light component may be done with reference to the time value of a pulse existing region. Also, the process of detecting individually signals of light-emitting particles from time series light intensity data may be conducted by an arbitrary way other than the above-mentioned way.

(ii) Calculation of the Polarization Characteristic Value of a Light-Emitting Particle (FIG. 3—Step 170)

Thus, when the signals of each light-emitting particle has been detected in the respective time series light intensity data of the s polarized light component and p polarized light component, a polarization characteristic value is computed for the light-emitting particle, using the light intensities of the s polarized light component and p polarized light component. As the light intensities Is and Ip of the s polarized light component and p polarized light component, for instance, the peak intensity, the integrated value of photon counts or the time integration value (the area of the shaded region of FIG. 2D) of a bell shaped function used in the fitting of the signal of the light-emitting particle detected in steps 130-160 may be selected. Further, for the polarization characteristic value, typically, the degree of polarization P, namely, $$P = (Ip - Is)/(Ip + Is) \quad (5)$$

may be used. In this regard, it may be other index values indicating a polarization characteristic, such as a light intensity value of the s polarized light component, the p polarized light component or a polarized light component in a certain specific direction, the light intensity ratio of the s polarized light component and p polarized light component, Ip/Is, an anisotropy of fluorescence (or phosphorescence), etc. Also, the polarization characteristic value may be computed using the average of the light intensity Is of the s polarized light components and the average of the light intensity Ip of the p polarized light components of detected light-emitting particles.

By the way, in measurement of the lights of the s polarized light component and p polarized light component in the device of FIG. 1A, it is possible that the detection sensitivity of the s polarized light component and the detection sensitivity of the p polarized light component are different from one another. For example, it is possible that the transmittances or the reflectances of the respective elements within the optical system change depending upon polarization directions, and also, the sensitivities of photodetectors 16s, p may differ from one another, and thus, it is possible that the detected value of the intensity of the s polarized light component and the detected value of the intensity of the p polarized light component are different from one another even when the lights of the same intensity are emitted from a light-emitting particle in the respective polarization directions. Then, preferably, in computing a polarization characteristic value, a treatment for correcting the difference between the detection sensitivity of the s polarized light component and the detection sensitivity of the p polarized light component may be performed. In performing this correction process, for example, the above-mentioned polarization degree P may be computed by the following expression:

[Expression 1]

$$P = \frac{\left(\frac{Ip}{Is}\right)C - 1}{\left(\frac{Ip}{Is}\right)C + 1} \quad (6)$$

where, C is a correcting value, which is the ratio of the intensity detected value Iso and the intensity detected value Ipo when the intensities of the p polarized light component and the s polarized light component of the light from a light-emitting particle are equal, Iso/Ipo (corresponding to the ratio of the detection sensitivity of the s polarized light component to the detection sensitivity of the p polarized light component). By assigning a value of a single light-emitting particle to the value of (Ip/Is) in Expression (6), the degree of polarization of the light-emitting particle is computed, and by assigning the total or the average of the intensity of two or more light-emitting particles, e.g., all the detected light-emitting particles to the value of (Ip/Is) in Expression (6), their average degree of polarization is computed.

The correcting value C can be computed, for example, through conducting the above-mentioned measurement of light for a fluorescent dye having a known degree of polarization and the detection of signals of the light-emitting particle (steps 100-160) and computing the p polarized component intensity Ip and s polarized component intensity Is of each light-emitting particle, by using the average (Ip/Is)av of those intensity ratios (Ip/Is) and the known degree of polarization Pk with:

[Expression 2]

$$C = \frac{1 + Pk}{\left(\frac{Ip}{Is}\right)_{av}(1 - Pk)} \quad (7)$$

Also, the correcting value C may be determined using the ratio of the intensity detected value Iso and the intensity detected value Ipo measured with non-polarized light as the excitation light.

Thus, according to the above-mentioned inventive optical analysis technique, in the scanning molecule counting method which detects a light-emitting particle individually by scanning a sample solution with a light detection region, it becomes possible to observe a polarization characteristic of a light-emitting particle. As noted, since a polarization characteristic is a physical quantity reflecting the size and shape of a particle, according to the present invention, it becomes possible to acquire the information on the size, structure or their change of an arbitrary particle to be observed or various intermolecular interaction by attaching a light emitting label with the particle to be observed to render it to be a light-emitting particle and observing a polarization characteristic of this light-emitting particle. Especially, in the present invention, since a polarization characteristic of a single light-emitting particle will be detected individually, it is expected that the observation of a polarization characteristic of a light-emitting particle of a low number density in a sample solution will be achieved.

In order to verify the validity of the present invention explained above, the experiments described below were conducted. In this regard, it should be understood that the following embodiments illustrate the validity of the present invention only, not intended to limit the scope of the present invention.

Embodiment 1

It was verified that a polarization characteristic of a light-emitting particle was observed by the present invention.

Using a fluorescent dye, TAMRA, and a plasmid stained with an intercalator fluorescent dye, SYTOX Orange as light-emitting particles, the polarization characteristics of these light-emitting particles were observed. For sample solutions, there were prepared a solution containing TAMRA at 10 pM (TAMRA solution) and a solution in which a plasmid (pBR322 and Takara Bio, Inc. Cat. No. 3035) was dissolved to be at 10 pM in a phosphate buffer (containing 0.05% Tween20) which contained SYTOX Orange (Invitrogen Corp., Cat. No. S-11368) at 10 nM (plasmid solution). In this connection, SYTOX Orange is a fluorescent dye whose fluorescence intensity increases about 500 times when it is bound with DNA (plasmid). In the light measurement, a single molecule fluorescence measuring apparatus MF20 (Olympus Corporation), equipped with the optical system of a confocal fluorescence microscope and a photon counting system, was used as the optical analysis device, and time series light intensity data (photon count data) of the s polarized light component and p polarized light component were simultaneously and separately acquired for the above-mentioned sample solutions in accordance with the manner explained in the above-mentioned "(2) Measurement of the light intensity of a sample solution". In that time, for both the TAMRA solution and the plasmid solution, a 543-nm laser light was used for excitation light, and, using a band pass filter, the light of the wavelength bands of 560 to 620 nm, was detected. Also, the polarization direction of the excitation light was set to become the same direction as the p polarized light component of the detected light. The moving speed of the light detection region in the sample solution was set to 15 mm/second; BIN TIME was set to 10 μsec.; and the measurement time was set to 2 seconds. After the light intensity measurement, in accordance with the procedures described in the above-mentioned "(3)(i) Detection of a signal corresponding to a light-emitting particle", the smoothing treatment was applied to the time series light intensity data acquired for the respective polarized light components with each sample solution, and after determining the start points and the end points of pulse signals in the smoothed data, the fitting of a Gauss function to each pulse signal was carried out by the least square method, and a peak intensity, a pulse width (full width at half maximum) and a correlation coefficient (in the Gauss function) were determined. Then, only the pulse signal satisfying the following conditions:

20 μsec.<pulse width<400 μsec.

Peak intensity>1.0*pc*/10 μsec.]

Correlation coefficient>0.95   (A)

was judged as a signal corresponding to a light-emitting particle, while a pulse signal which did not satisfy the above-mentioned conditions was disregarded as noise.

FIGS. 6A and 6B each show diagram in which the p polarized component intensities Ip of signals of individual light-emitting particles detected with the TAMRA solution and the plasmid solution are plotted against the s polarized component intensity Is of the corresponding signal (For each of the intensities Is and Ip, the time integration value of the bell shaped function having been fit to the signal of a light-emitting particle were used). With reference to the diagrams, the plots of the p polarized component intensity Ip against the s polarized component intensity Is are distributed almost on a straight line, and for the TAMRA solution, the average (Ip/Is)av of the ratio Ip/Is of the p polarized component intensity Ip to the s polarized component intensity Is [the gradient of the plots of the p polarized component intensity Ip to the s polarized component intensity Is] was 1.314 and for the plasmid solution, (Ip/Is) av was 2.902. This suggests that the intensity ratio of the polarized light components (one example of polarization characteristic values) detected according to the present invention is a value specific to a particle, showing a polarization characteristic of the light-emitting particle.

Furthermore, since it has been known that the degree of polarization P of the fluorescent dye, TAMRA, is 0.034, The correcting value C in Expression (7) was computed as C=0.815 with Expression (8) using this degree of polarization P and the above-mentioned (Ip/Is)av (=1.314) computed from the measurement result with the TAMRA solution. Using this correction value C, the degree of polarization P of the plasmid computed with Expression (7) with (Ip/Is)av (=2.902) computed from the measurement result with the plasmid solution was 0.406.

Thus, as understood from the results of the above-mentioned embodiment, according to the above-mentioned inventive optical analysis technique, a polarization characteristic of a light-emitting particle can be observed in the scanning molecule counting method. Especially, the inventive optical analysis technique is designed to detect individually a polarized light component of a single light-emitting particle and compute its polarization characteristic value, and therefore, according to the present invention, even when the light-emitting particle concentration in a sample solution is lower than the concentration range requested in optical analysis techniques, such as FCS and FIDA-PO, the observation of a polarization characteristic of a light-emitting particle is possible, and this feature is advantageous in conducting an analysis of a rare or expensive sample often used in the field of the research and development of Medicine and/or Biology.

The invention claimed is:

1. An optical analysis device which detects and analyzes light from a light-emitting particle dispersed and moving at random in a sample solution using an optical system of a confocal microscope or a multiphoton microscope, comprising:
    a light detection region moving portion which moves a position of a light detection region of the optical system in the sample solution by changing an optical path of the optical system;
    a light irradiating portion which irradiates the light detection region with excitation light including a predetermined polarized light component;
    a light detecting portion which detects an intensity of at least one polarized light component of light from the light detection region; and
    a signal processing portion which generates a time series light intensity data of the at least one polarized light component of the light from the light detection region detected by the light detecting portion while moving the position of the light detection region in the sample solution, detects individually a signal from each light-emitting particle in the intensity of the at least one polarized light component of the light detected with the light detection portion with moving the position of the light detection region in the sample solution by detecting individually in the time series light intensity data, as the signal of one light-emitting particle, a variation in time of a light intensity having a profile expected in the light from one light-emitting particle which moves relatively in an inside of the light detection region, and computes, based on the intensity of the at least one polarized light component of the signal of the light of the detected light-emitting particle, a polarization characteristic value of the light-emitting particle.

2. The device of claim 1, wherein the light detecting portion measures independently intensities of an s polarized light component and a p polarized light component in the light from the light detection region; and the polarization characteristic value is computed based on the intensity of the s polarized light component and the intensity of the p polarized light component of the signal of the light of the light-emitting particle.

3. The device of claim 1, wherein the at least one polarized light component of the light from the light detection region is extracted from the light from the light detection region using a polarization beam splitter.

4. The device of claim 1, wherein the polarization characteristic value is a degree of polarization.

5. The device of claim 1, wherein the light detecting portion measures independently intensity of an s polarized light component and intensity of a p polarized light component in the light from the light detection region; and the signal processing portion computes the polarization characteristic value based on a detected value of the intensity of the s polarized light component and a detected value of the intensity of the p polarized light component of the signal of the light of the light-emitting particle, using a correcting value which corrects a difference between a detection sensitivity of the intensity of the s polarized light component and a detection sensitivity of the intensity of the p polarized light component.

6. The device of claim 1, wherein the signal processing portion uses a time integration value of a bell shaped function fit to a time change of the intensity of the at least one polarized light component of the signal of the light of the light-emitting particle in computing the polarization characteristic value of the light-emitting particle.

7. The device of claim 1, wherein the signal processing portion uses a time integration value of the intensity of the at least one polarized light component of the signal of the light of the light-emitting particle in computing the polarization characteristic value of the light-emitting particle.

8. The device of claim 1, wherein the signal processing portion counts a number of the signals of the lights of the light-emitting particles detected individually to count a number of the light-emitting particles detected during the moving of the position of the light detection region.

9. The device of claim 1, wherein the light detection region moving portion moves the position of the light detection region at a velocity quicker than a diffusion moving velocity of the light-emitting particle.

10. An optical analysis method of detecting light from a light-emitting particle dispersed and moving at random in a sample solution using an optical system of a confocal microscope or a multiphoton microscope, comprising steps of:
    moving a position of a light detection region of the optical system in the sample solution by changing an optical path of the optical system;
    irradiating the light detection region with excitation light including a predetermined polarized light component;
    detecting an intensity of at least one polarized light component of light from the light detection region with moving the position of the light detection region in the sample solution;
    generating a time series light intensity data of the at least one polarized light component of the light from the light detection region detected while moving the position of the light detection region in the sample solution;
    detecting a signal from each light-emitting particle individually in the intensity of the at least one polarized light component of the detected light by detecting individually in the time series light intensity data, as the signal of one light-emitting particle, a variation in time of a light intensity having a profile expected in the light from one light-emitting particle which moves relatively in an inside of the light detection region;
    and computing, based on the intensity of the at least one polarized light component of the detected signal of the light of the light-emitting particle, a polarization characteristic value of the light-emitting particle.

11. The method of claim 10, wherein, in the step of detecting an intensity of at least one polarized light component of light from the light detection region, intensities of an s polarized light component and a p polarized light component in the light from the light detection region are separately measured; and in the step of computing a polarization characteristic value of the light-emitting particle, the polarization characteristic value is computed based on the intensity of the s polarized light component and the intensity of the p polarized light component of the signal of the light of the light-emitting particle.

12. The method of claim 10, wherein the at least one polarized light component of the light from the light detection region is extracted from the light from the light detection region using a polarization beam splitter.

13. The method of claim 10, wherein the polarization characteristic value is a degree of polarization.

14. The method of claim 10, wherein, in the step of detecting an intensity of at least one polarized light component of the light from the light detection region, an intensity of an s polarized light component and an intensity of a p polarized light component in the light from the light detection region are separately measured; and in the step of computing a polarization characteristic value of the light-emitting particle, the polarization characteristic value is computed based on a detected value of the intensity of the s polarized light component and a detected value of the intensity of the p polarized light component of the signal of the light of the light-emitting particle, using a correcting value which corrects a difference between a detection sensitivity of the intensity of the s polarized light component and a detection sensitivity of the intensity of the p polarized light component.

15. The method of claim 10, wherein a time integration value of a bell shaped function fit to a time change of the intensity of the at least one polarized light component of the signal of the light of the light-emitting particle is used in computing the polarization characteristic value of the light-emitting particle.

16. The method of claim 10, wherein a time integration value of the intensity of the at least one polarized light component of the signal of the light of the light-emitting particle is used in computing the polarization characteristic value of the light-emitting particle.

17. The method of claim 10, comprising further a step of counting a number of the signals of the lights of the light-emitting particles detected individually to count a number of the light-emitting particles detected during the moving of the position of the light detection region.

18. The method of either of claims 10 to 17, wherein, in the step of moving the position of the light detection region, the position of the light detection region is moved at a velocity quicker than a diffusion moving velocity of the light-emitting particle.

19. A computer readable storage device having a computer program product including programmed instructions for optical analysis for detecting light from a light-emitting particle dispersed and moving at random in a sample solution using an optical system of a confocal microscope or a multiphoton microscope, said programmed instructions causing a computer to perform steps comprising:
    moving a position of a light detection region of the optical system in the sample solution by changing an optical path of the optical system;
    irradiating the light detection region with excitation light including a predetermined polarized light component;
    detecting an intensity of at least one polarized light component of light from the light detection region with moving the position of the light detection region in the sample solution; and
    generating a time series light intensity data of the at least one polarized light component of the light from the light detection region detected while moving the position of the light detection region in the sample solution;
    detecting a signal from each light-emitting particle individually in the intensity of the at least one polarized light component of the detected light by detecting individually in the time series light intensity data, as the signal of one light-emitting particle, a variation in time of a light intensity having a profile expected in the light from one light-emitting particle which moves relatively in an inside of the light detection region;

and computing, based on the intensity of the at least one polarized light component of the detected signal of the light of the light-emitting particle, a polarization characteristic value of the light-emitting particle.

20. The computer readable storage device of claim 19, wherein, in the step of detecting an intensity of at least one polarized light component of the light from the light detection region, intensities of an s polarized light component and a p polarized light component in the light from the light detection region are separately measured; and in the step of computing a polarization characteristic value of the light-emitting particle, the polarization characteristic value is computed based on the intensity of the s polarized light component and the intensity of the p polarized light component of the signal of the light of the light-emitting particle.

21. The computer readable storage device of claim 19, wherein the polarization characteristic value is a degree of polarization.

22. The computer readable storage device of claim 19, wherein, in the step of detecting an intensity of at least one polarized light component of the light from the light detection region, an intensity of an s polarized light component and an intensity of a p polarized light component in the light from the light detection region are separately measured; and in the step of computing a polarization characteristic value of the light-emitting particle, the polarization characteristic value is computed based on a detected value of the intensity of the s polarized light component and a detected value of the intensity of the p polarized light component of the signal of the light of the light-emitting particle, using a correction value which corrects a difference between a detection sensitivity of the intensity of the s polarized light component and a detection sensitivity of the intensity of the p polarized light component.

23. The computer readable storage device of claim 19, wherein a time integration value of a bell shaped function fit to a time change of the intensity of the at least one polarized light component of the signal of the light of the light-emitting particle is used in computing the polarization characteristic value of the light-emitting particle.

24. The computer readable storage device of claim 19, wherein a time integration value of the intensity of the at least one polarized light component of the signal of the light of the light-emitting particle is used in computing the polarization characteristic value of the light-emitting particle.

25. The computer readable storage device of claim 19, comprising further a step of counting a number of the signals of the lights of the light-emitting particles detected individually to count a number of the light-emitting particles detected during the moving of the position of the light detection region.

26. The computer readable storage device of either of claim 19, wherein, in the step of moving the position of the light detection region, the position of the light detection region is moved at a velocity quicker than a diffusion moving velocity of the light-emitting particle.

* * * * *